US009775821B2

(12) United States Patent
Hallam et al.

(10) Patent No.: US 9,775,821 B2
(45) Date of Patent: *Oct. 3, 2017

(54) COMPOSITIONS FOR THE TREATMENT OF AUTODIGESTION

(71) Applicant: Leading BioSciences, Inc., Solana Beach, CA (US)

(72) Inventors: Thomas Hallam, New York, NY (US); Robin Jackman, San Diego, CA (US); John Rodenrys, La Jolla, CA (US)

(73) Assignee: Leading BioSciences, Inc., Solana Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,860

(22) Filed: Mar. 14, 2016

(65) Prior Publication Data

US 2016/0263064 A1    Sep. 15, 2016

Related U.S. Application Data

(63) Continuation of application No. 14/666,926, filed on Mar. 24, 2015, now Pat. No. 9,314,442.

(Continued)

(51) Int. Cl.
| | | |
|---|---|---|
| *A61K 31/195* | (2006.01) |
| *A61K 31/7004* | (2006.01) |
| *A61K 47/26* | (2006.01) |
| *A61K 47/10* | (2017.01) |
| *A61K 31/196* | (2006.01) |
| *A61K 9/00* | (2006.01) |
| *A61K 31/00* | (2006.01) |
| *A61K 9/08* | (2006.01) |

(Continued)

(52) U.S. Cl.
CPC .......... *A61K 31/195* (2013.01); *A61K 9/0019* (2013.01); *A61K 9/0053* (2013.01); *A61K 9/08* (2013.01); *A61K 31/00* (2013.01); *A61K 31/196* (2013.01); *A61K 31/7004* (2013.01); *A61K 33/00* (2013.01); *A61K 33/04* (2013.01); *A61K 33/14* (2013.01); *A61K 47/10* (2013.01); *A61K 47/26* (2013.01)

(58) Field of Classification Search
CPC .. A61K 31/195; A61K 31/7004; A61K 47/10; A61K 47/26
See application file for complete search history.

(56) References Cited

U.S. PATENT DOCUMENTS

| | | |
|---|---|---|
| 4,465,662 A | 8/1984 | Sato et al. |
| 5,962,405 A | 10/1999 | Seelich |

(Continued)

FOREIGN PATENT DOCUMENTS

| | | |
|---|---|---|
| CN | 103054861 A | 4/2013 |
| CN | 103099800 A | 5/2013 |

(Continued)

OTHER PUBLICATIONS

Altschuler (2013). "Degrading proteases and organ failure during physiological shock," Ph.D. Dissertation; University of California, San Diego.

(Continued)

*Primary Examiner* — Timothy Thomas
(74) *Attorney, Agent, or Firm* — Mintz Levin Cohn Ferris Glovsky and Popeo, P.C.

(57) ABSTRACT

Compositions for the treatment of shock, autodigestion, multi-organ failure, intestinal ischemia, or intestinal hypoperfusion are provided.

11 Claims, 10 Drawing Sheets

Related U.S. Application Data

(60) Provisional application No. 62/019,007, filed on Jun. 30, 2014, provisional application No. 61/970,247, filed on Mar. 25, 2014.

(51) Int. Cl.
*A61K 33/00* (2006.01)
*A61K 33/04* (2006.01)
*A61K 33/14* (2006.01)

(56) References Cited

U.S. PATENT DOCUMENTS

| | | | |
|---|---|---|---|
| 6,017,881 | A | 1/2000 | Ammons et al. |
| 6,121,232 | A | 9/2000 | Nur et al. |
| 6,534,283 | B1 | 3/2003 | Schmid-Schoenbein et al. |
| 6,708,822 | B1 | 3/2004 | Muni |
| 6,939,559 | B1 | 9/2005 | Nishibe et al. |
| 7,235,247 | B2 | 6/2007 | Nishibe et al. |
| 7,276,235 | B2 | 10/2007 | Metzner et al. |
| 8,252,302 | B2 | 8/2012 | Macdonald |
| 8,541,371 | B2 | 9/2013 | Schmid-Schonbein et al. |
| 8,957,113 | B2 | 2/2015 | Moore et al. |
| 9,278,077 | B2 | 3/2016 | DeBrouse |
| 9,314,442 | B2 | 4/2016 | Hallam et al. |
| 2002/0001584 | A1 | 1/2002 | Metzner et al. |
| 2003/0144212 | A1 | 7/2003 | Hoffman et al. |
| 2004/0018984 | A1 | 1/2004 | Miyazaki |
| 2006/0198817 | A1 | 9/2006 | Alverdy |
| 2007/0059272 | A1 | 3/2007 | Alverdy |
| 2008/0194611 | A1 | 8/2008 | Alverdy |
| 2008/0206188 | A1 | 8/2008 | Alverdy et al. |
| 2009/0017114 | A1 | 1/2009 | Heasley |
| 2009/0186949 | A1 | 7/2009 | Alverdy |
| 2009/0324736 | A1 | 12/2009 | Johnson et al. |
| 2010/0179091 | A1 | 7/2010 | Schmid-Schonbein et al. |
| 2011/0060040 | A1 | 3/2011 | Virsik et al. |
| 2012/0078017 | A1 | 3/2012 | Alverdy et al. |
| 2012/0316190 | A1 | 12/2012 | Alverdy |
| 2013/0310325 | A1 | 1/2013 | Schmid-Schonbein et al. |
| 2014/0018293 | A1 | 1/2014 | Delano et al. |
| 2014/0271923 | A1 | 9/2014 | Reid |
| 2015/0290157 | A1 | 10/2015 | Moore et al. |
| 2015/0297619 | A1 | 10/2015 | Schmid-Schonbein et al. |

FOREIGN PATENT DOCUMENTS

| | | |
|---|---|---|
| CN | 103565743 A | 2/2014 |
| EP | 1567117 B1 | 2/2012 |
| JP | 2009-019008 A | 1/2009 |
| WO | WO-99/08514 A1 | 2/1999 |
| WO | WO-01/37854 A1 | 5/2001 |
| WO | WO-2004/047778 A1 | 6/2004 |
| WO | WO-2006/073430 A2 | 7/2006 |
| WO | WO-2006/132963 A2 | 12/2006 |
| WO | WO-2006/132963 A3 | 12/2006 |
| WO | WO-2007/053194 A2 | 5/2007 |
| WO | WO-2007/053194 A3 | 5/2007 |
| WO | WO-2007/101264 A2 | 9/2007 |
| WO | WO-2007/101264 A3 | 9/2007 |
| WO | WO-2009/045543 A1 | 4/2009 |
| WO | WO-2009/132149 A2 | 10/2009 |
| WO | WO-2010/087874 A1 | 8/2010 |
| WO | WO-2012/040595 A2 | 3/2012 |
| WO | WO-2012/045083 A2 | 4/2012 |
| WO | WO-2013/093164 A1 | 6/2013 |
| WO | WO-2014/028052 A1 | 2/2014 |
| WO | WO-2015/148474 A1 | 10/2015 |

OTHER PUBLICATIONS

Altshuller et al. Poster—Development of Strategies to Minimize Autodigestion and Death: Methods to Preserve the Barrier of an Ischemic Intestine. UCSD Jacobs School of Engineering Research Expo. Apr. 18, 2013.
Altshuler et al. Transmural intestinal wall permeability in severe ischemia after enteral protease inhibition. PLoS One 9(5)e96655 (2014).
CN 103054861-A; English machine translation supplied by Espacenet on Jul. 20, 2015.
Chang et al. Breakdown of mucin as barrier to digestive enzymes in the ischemic rat small intestine. PLos One 7(6):e40087 (2012).
Chang et al. Disruption of the mucosal barrier during gut ischemia allows entry of digestive enzymes into the intestinal wall. Shock 37(3):297-305 (2012).
Delano et al. Blockade of Pancreatic Digestive Proteases in Severe Hemorrhagic Shock Enhances Long-term Survival Rate. Experimental Biology Annual Meeting. 43:594 (Abstract) (2009).
Delano, F.A. et al. (Jan. 23, 2013). "Pancreatic digestive enzyme blockade in the intestine increases survival after experimental shock," Sci Transl Med 5(169): 169ra11.
Delano et al. Pancreatic digestive enzyme blockade in the small intestine prevents insulin resistance in hemorrhagic shock. Shock 41(1):55-61 (2014).
GoLYTELY Product Insert; 2013.
Kim et al. Inhibition of Intraluminal Pancreatic Enzymes With Nafamostat Mesilate Improves Clinical Outcomes After Hemorrhagic Shock in Swine. Injury, Infection, and Critical Care 68(5):1078-1083 (2010).
Lee et al. Successful treatment with continuous enteral protease inhibitor in a patient with severe septic shock. Transplant Proc 44(3):817-819 (2012).
Mitsuoka et al. Generation of in vivo activating factors in the ischemic intestine by pancreatic enzymes. PNAS 97(4):1772-1777 (2000).
Mooney, R.A. et al. (1976). "Prevention of peritoneal adhesions with aprotinin (trasylol)," *J Int Med Res* 495):360-363.
PCT/US2015/022198 International Search Report and Written Opinion mailed Jun. 15, 2015.
PCT/US2011/053019 International Preliminary Report on Patentability dated Apr. 4, 2013.
PCT/US2011/053019 International Search Report and Written Opinion dated Apr. 10, 2012.
U.S. Appl. No. 13/825,779 Office Action dated Apr. 2, 2015.
U.S. Appl. No. 13/825,779 Office Action dated Sep. 26, 2014.
Wu et al. High-Molecule-Weigh Polyethylene Glycol Prevents Lethal Sepsis Due to Intestinal Pseudomons aeruginosa. Gastronterology 126:488-498 (2004).
Lan Wang et al. (2009). "Use of glucose-electrolyte effervescent in autumn diarrhea diseases," located at <http://big.hi138.com/yiyao/yaoxue/200908/132939.asp>, 3 pages. (Translation of Abstract only).

COMPOSITIONS FOR THE TREATMENT OF AUTODIGESTION

CROSS-REFERENCE TO RELATED APPLICATIONS

This application is a continuation of U.S. Application Ser. No. 14/666,926, filed Mar. 24, 2015, issued as U.S. Pat. No. 9,314,442, which claims priority to U.S. Application No. 61/970,247, filed Mar. 25, 2014, and U.S. Application No. 62/019,007, filed Jun. 30, 2014, each of which is incorporated herein by reference in its entirety.

BACKGROUND OF THE INVENTION

Shock is a life-threatening condition that can result from trauma, severe blood loss, heart attacks, cardiovascular dysfunction, ischemia, sepsis, and burns. Major classes of shock include but are not limited to cardiogenic shock, hypovolemic shock, hemorrhagic shock, anaphylactic shock, neurogenic shock, and septic (or endotoxic) shock. Shock can lead to multi-organ failure (also known as multi-organ dysfunction syndrome) if immediate medical treatment is not received. Under the conditions of shock, the intestinal barrier and walls become compromised and the digestive enzymes that are normally contained within the intestine permeate through the intestinal walls and enter the bloodstream, leading to a condition known as autodigestion, in which the body's digestive enzymes begin to digest its own tissues. Autodigestion is hypothesized to be a mechanism for inflammation and multi-organ failure resulting from shock.

SUMMARY OF THE INVENTION

Despite the severity of shock, autodigestion, multi-organ failure, ischemia, and hypoperfusion, few therapies are available. Most efforts have focused on the modulation of individual inflammatory mediators of shock, e.g., cytokines, nitric oxide, and endotoxin, to mitigate the effects of shock. However, therapies that target particular inflammatory mediators have proven largely ineffective due to the multi-faceted nature of the mediators. Thus, a need exists for therapeutics to treat shock, autodigestion, multi-organ failure, ischemia, and hypoperfusion, particularly therapeutics that preserve or help reestablish the integrity of the intestinal wall.

Disclosed herein are compositions for the treatment of shock, autodigestion, multi-organ failure, intestinal ischemia, and/or hypoperfusion. In some embodiments, compositions disclosed herein comprise tranexamic acid, PEG, glucose, and one or more electrolytes. In some embodiments, the PEG is PEG 3350. In certain embodiments, compositions disclosed herein comprise a non-colonic cleansing amount of PEG 3350. In some embodiments, compositions disclosed herein comprise about 7.8 g of tranexamic acid, about 50.3 g of PEG 3350, about 40 g of glucose, about 5.7 g of sodium sulfate, about 1.7 g of sodium bicarbonate, about 1.5 g of sodium chloride, and about 0.7 g of potassium chloride. In some embodiments, compositions disclosed herein comprise about 7.8 g of tranexamic acid and about 40 g of glucose. In some embodiments, compositions disclosed herein are formulated as aqueous solutions. In certain specific embodiments, the volume of the aqueous solution is 1000 mL. In some embodiments, compositions disclosed herein comprise about 7.5 g of tranexamic acid, about 32.5 g of PEG 3350, about 28 g of glucose, about 4.0 g of sodium sulfate, about 1.2 g of sodium bicarbonate, about 1.0 g of sodium chloride, and about 0.5 g of potassium chloride. In some embodiments, compositions disclosed herein comprise about 7.5 g of tranexamic acid and about 28 g of glucose. In some embodiments, compositions disclosed herein are formulated as aqueous solutions. In certain specific embodiments, the volume of the aqueous solution is 700 mL.

In some embodiments, compositions disclosed herein are administered for the treatment of shock, autodigestion, multi-organ failure, intestinal ischemia, or hypoperfusion. In certain specific embodiments, compositions disclosed herein are administered for the treatment of cardiogenic shock, hemorrhagic shock, or septic shock. In some embodiments, compositions disclosed herein are administered for the treatment of septic shock associated with or caused by sepsis. In some embodiments, compositions disclosed herein are administered for the treatment of cardiogenic shock associated with or caused by cardiovascular surgery, myocardial infarction, arrhythmia, or mechanical complications. In some embodiments, compositions disclosed herein are administered for the treatment of hemorrhagic shock associated with or caused by trauma. In some embodiments, compositions disclosed herein are administered for the treatment of shock associated with or caused by a hemorrhagic virus. In some embodiments, the hemorrhagic virus is an Ebola virus. In some embodiments, compositions disclosed herein are administered orally, or via a nasogastric, orogastric, nasojejunal, orojejunal, nasoduodenal, or percutaneous endoscopic gastrostomy tube or catheter.

In some embodiments, disclosed herein is a kit comprising: the components tranexamic acid, PEG, glucose, and one or more electrolytes, wherein at least one of the components tranexamic acid, PEG, glucose, and one or more electrolytes is in a separate container from at least one of the other components tranexamic acid, PEG, glucose, and one or more electrolytes; and instructions to combine the components tranexamic acid, PEG, glucose, and one or more electrolytes in a single composition. In some embodiments, a kit comprises tranexamic acid, PEG, and one or more electrolytes are in a first container, and glucose in a second container. In some embodiments, a kit comprises instructions to reconstitute the components with water to provide an aqueous formulation. In some embodiments, a kit comprises a first container comprising about 7.8 g of tranexamic acid, about 50.3 g of PEG 3350, about 5.7 g of sodium sulfate, about 1.7 g of sodium bicarbonate, about 1.5 g of sodium chloride, and about 0.7 g of potassium chloride, and a second container comprising about 40 g of glucose. In some embodiments, a kit comprises a first container comprising about 7.8 g of tranexamic acid, about 50.3 g of PEG 3350, about 5.7 g of sodium sulfate, about 1.7 g of sodium bicarbonate, about 1.5 g of sodium chloride, and about 0.7 g of potassium chloride, a second container comprising about 40 g of glucose, and instructions to reconstitute the tranexamic acid, PEG, glucose, and one or more electrolytes with water to 1000 mL. In some embodiments, a kit comprises a first container comprising about 7.5 g of tranexamic acid, about 32.5 g of PEG 3350, about 4.0 g of sodium sulfate, about 1.2 g of sodium bicarbonate, about 1.0 g of sodium chloride, and about 0.5 g of potassium chloride, and a second container comprising about 28 g of glucose. In some embodiments, a kit comprises a first container comprising about 7.5 g of tranexamic acid, about 32.5 g of PEG 3350, about 4.0 g of sodium sulfate, about 1.2 g of sodium bicarbonate, about 1.0 g of sodium chloride, and about 0.5 g of potassium chloride, a second container comprising about 28 g of glucose, and instructions to reconstitute the tranexamic acid, PEG, glucose, and one or more electrolytes with water to 700 mL. In some embodiments, a kit comprises instructions to administer the combined components orally or via a nasogastric, orogastric, nasojejunal, orojejunal, nasoduodenal, or percutaneous endoscopic gastrostomy tube or catheter.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows that rat intestinal villi appear healthy and structurally intact and that the entire length of the villi is visible and completely covered in goblet cells, following administration of Representative Formulation 1 and shock induction according to Example 2. FIG. 2B shows that rat intestinal villi are structurally damaged, with missing villi tips and atypical goblet cell staining, following administration of Comparative Formulation 1 and shock induction according to Example 2.

FIG. 4A shows that villi appear healthy and structurally intact and that the entire length of the villi is visible and completely covered in goblet cells, following administration of Representative Formulation 2 and shock induction according to Example 3. FIG. 4B shows that rat villi are structurally damaged, with missing villi tips and atypical goblet cell staining, following administration of Comparative Formulation 2 and shock induction according to Example 3.

FIG. 6A shows that villi appear healthy and structurally intact and that the entire length of the villi is visible and completely covered in goblet cells, following administration of Representative Formulation 3 and hemorrhagic shock induction according to Example 4. FIG. 6B shows that rat villi are structurally damaged following administration of Comparative Formulation 3 and hemorrhagic shock induction according to Example 4.

DETAILED DESCRIPTION OF THE INVENTION

Figure 1:
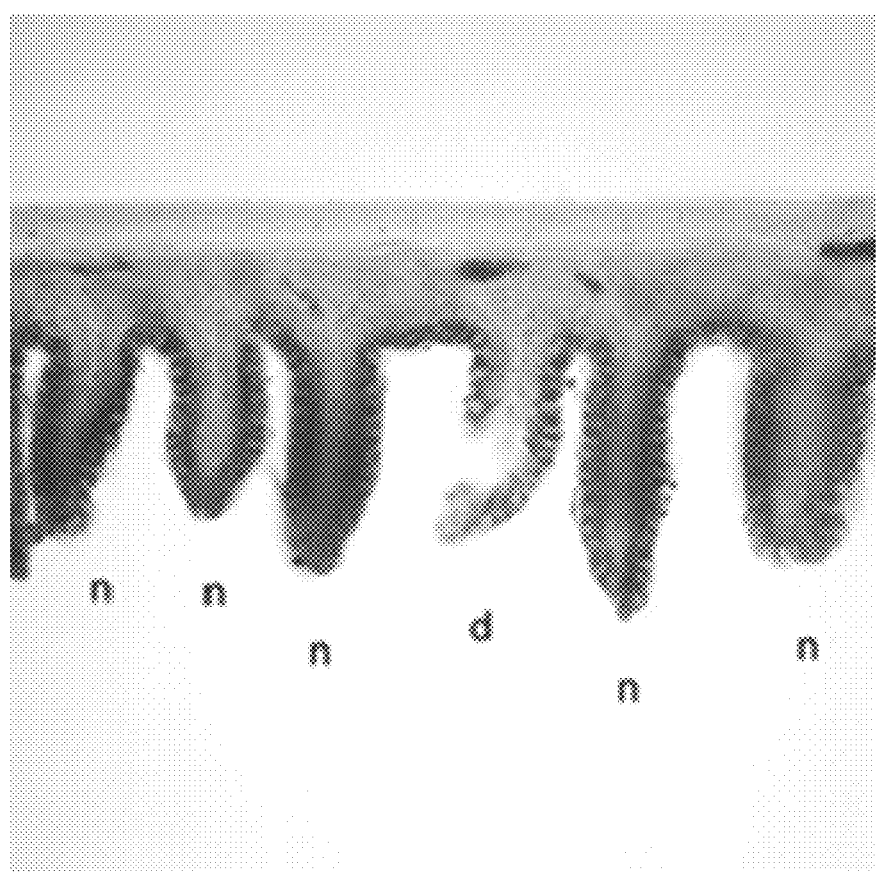
FIG. 1 shows a representative cross section of the small intestine from a rat treated with an enteral formulation and superior mesentery artery occlusion (SMAO). Healthy villi are marked with n and damaged villi are marked with d.

Unless defined otherwise, all technical and scientific terms used herein have the same meaning as commonly understood by one of skill in the art to which the inventions described herein belong. All publications, patents, and patent applications mentioned in this specification are hereby incorporated by reference to the same extent as if each individual publication, patent, or patent application was specifically and individually indicated to be incorporated by reference.

Definition of Terms

When the term "about" is present before a numerical value herein, it means±10% of the numerical value. For example, as used herein, the term "about 10 g" means an amount from 9 g to 11 g.

As used herein, the terms "comprising," "including," "such as," and "for example" (or "e.g.") are used in their open, non-limiting sense.

The term "treat" and its grammatical variants (e.g., "to treat," "treating," and "treatment") refer to administration of an active pharmaceutical ingredient to a patient with the purpose of ameliorating or reducing the incidence of one or more symptoms of a condition or disease state in the patient. In some embodiments, such symptoms are chronic or acute, and such amelioration are partial or complete for some instances. In the present context, treatment entails administering a pharmaceutical composition described herein to a patient via a route of administration disclosed herein.

As used herein, "PEG" refers to a polyethylene glycol polymer. When "PEG" is used in combination with a numerical value, the numerical value defines the average molecular weight of the polyethylene glycol polymer. For an example PEG 3350 refers to a polyethylene glycol polymer that has an average molecular weight of 3,350 Da.

As used herein, the term "non-colonic cleansing amount" refers to an amount of a substance that does not cause significant or substantially all removal of feces and toxins from the colon and intestinal tract when administered to the gastrointestinal tract.

As used herein, the terms "electrolyte" and "electrolytes" are used to describe any substances that ionize when dissolved in an ionizing solvent, such as water. Electrolytes include, but are not limited to, soluble salts, acids, or bases.

As used herein, the term "wt %" refers to the weight percent of a given component in a composition. For example, as used herein, an aqueous solution comprising 4 wt % glucose refers to an aqueous solution that comprises 4 grams of glucose per 100 grams of the solution.

Compositions

Disclosed herein are compositions for the treatment of shock, autodigestion, multi-organ failure, intestinal ischemia, or hypoperfusion. In some embodiments, compositions disclosed herein comprise tranexamic acid. In some embodiments, the compositions comprise about 7.0 g, about 7.1 g, about 7.2 g, about 7.3 g, about 7.4 g, about 7.5 g, about 7.6 g, about 7.7 g, about 7.8 g, about 7.9 g, about 8.0 g, about 8.1 g, about 8.2 g, about 8.3 g, about 8.4 g, about 8.5 g, or about 8.6 g of tranexamic acid. In a specific embodiment, compositions disclosed herein comprise about 7.8 g of tranexamic acid. In some embodiments, compositions disclosed herein comprise about 7.0 g to about 8.6 g of tranexamic acid.

In some embodiments, the compositions disclosed herein comprise about 6.8 g, about 6.9 g, about 7.0 g, about 7.1 g, about 7.2 g, about 7.3 g, about 7.4 g, about 7.5 g, about 7.6 g, about 7.7 g, about 7.8 g, about 7.9 g, about 8.0 g, about 8.1 g, about 8.2 or about 8.3 g of tranexamic acid. In a specific embodiment, compositions disclosed herein comprise about 7.5 g of tranexamic acid. In some embodiments, compositions disclosed herein comprise about 6.8 g to about 8.3 g of tranexamic acid.

In some embodiments, compositions disclosed herein comprise a non-colonic cleansing amount of PEG. In certain specific embodiments, compositions disclosed herein comprise a non-colonic cleansing amount of PEG 2000, PEG 3000, PEG 3350, or PEG 4000. In a specific embodiment, compositions disclosed herein comprise a non-colonic cleansing amount of PEG 3350. In some embodiments, a non-colonic cleansing amount of PEG, e.g., PEG 3350, is about 33.9 g, about 34.0 g, about 34.1 g, about 34.2 g, about 34.3 g, about 34.4 g, about 34.5 g, about 34.6 g, about 34.7 g, about 34.8 g, about 34.9 g, about 35.0 g, about 35.1 g, about 35.2 g, about 35.3 g, about 35.4 g, about 35.5 g, about 35.6 g, about 35.7 g, about 35.8 g, about 35.9 g, about 36.0 g, about 36.1 g, about 36.2 g, about 36.3 g, about 36.4 g, about 36.5 g, about 36.6 g, about 36.7 g, about 36.8 g, about 36.9 g, about 37.0 g, about 37.1 g, about 37.2 g, about 37.3 g, about 37.4 g, about 37.5 g, about 37.6 g, about 37.7 g, about 37.8 g, about 37.9 g, about 38.0 g, about 38.1 g, about 38.2 g, about 38.3 g, about 38.4 g, about 38.5 g, about 38.6 g, about 38.7 g, about 38.8 g, about 38.9 g, about 39.0 g, about 39.1 g, about 39.2 g, about 39.3 g, about 39.4 g, about 39.5 g, about 39.6 g, about 39.7 g, about 39.8 g, about 39.9 g, about 40.0 g, about 40.1 g, about 40.2 g, about 40.3 g, about 40.4 g, about 40.5 g, about 40.6 g, about 40.7 g, about 40.8 g, about 40.9 g, about 41.0 g, about 41.1 g, about 41.2 g, about 41.3 g, about 41.4 g, about 41.5 g, about 41.6 g, about 41.7 g, about 41.8 g, about 41.9 g, about 42.0 g, about 42.1 g, about 42.2 g, about 42.3 g, about 42.4 g, about 42.5 g, about 42.6 g, about 42.7 g, about 42.8 g, about 42.9 g, about 43.0 g, about 43.1 g, about 43.2 g, about 43.3 g, about 43.4 g, about 43.5 g, about 43.6 g, about 43.7 g, about 43.8 g, about 43.9 g, about 44.0 g, about 44.1 g, about 44.2 g, about 44.3 g, about 44.4 g, about 44.5 g, about 44.6 g, about 44.7 g, about 44.8 g, about 44.9 g, about 45.0 g, about 45.1 g, about 45.2 g, about 45.3 g, about 45.4 g, about 45.5 g, about 45.6 g, about 45.7 g, about 45.8 g, about 45.9 g, about 46.0 g, about 46.1 g, about 46.2 g, about 46.3 g, about 46.4 g, about 46.5 g, about 46.6 g, about 46.7 g, about 46.8 g, about 46.9 g, about 47.0 g, about 47.1 g, about 47.2 g, about 47.3 g, about 47.4 g, about 47.5 g, about 47.6 g, about 47.7 g, about 47.8 g, about 47.9 g, about 48.0 g, about 48.1 g, about 48.2 g, about 48.3 g, about 48.4 g, about 48.5 g, about 48.6 g, about 48.7 g, about 48.8 g, about 48.9 g, about 49.0 g, about 49.1 g, about 49.2 g, about 49.3 g, about 49.4 g, about 49.5 g, about 49.6 g, about 49.7 g, about 49.8 g, about 49.9 g, about 50.0 g, about 50.1 g, about 50.2 g, about 50.3 g, about 50.4 g, about 50.5 g, about 50.6 g, about 50.7 g, about 50.8 g, about 50.9 g, about 51.0 g, about 51.1 g, about 51.2 g, about 51.3 g, about 51.4 g, about 51.5 g, about 51.6 g, about 51.7 g, about 51.8 g, about 51.9 g, about 52.0 g, about 52.1 g, about 52.2 g, about 52.3 g, about 52.4 g, about 52.5 g, about 52.6 g, about 52.7 g, about 52.8 g, about 52.9 g, about 53.0 g, about 53.1 g, about 53.2 g, about 53.3 g, about 53.4 g, about 53.5 g, about 53.6 g, about 53.7 g, about 53.8 g, about 53.9 g, about 54.0 g, about 54.1 g, about 54.2 g, about 54.3 g, about 54.4 g, about 54.5 g, about 54.6 g, about 54.7 g, about 54.8 g, about 54.9 g, about 55.0 g, about 55.1 g, about 55.2 g, or about 55.3 g. In a specific embodiment, a non-colonic cleansing amount of PEG, e.g., PEG 3350 is about 50.3 g. In some embodiments, a non-colonic cleansing amount of PEG, e.g., PEG 3350, is about 45.2 g to about 55.3 g. In a specific embodiment, a non-colonic cleansing amount of PEG, e.g., PEG 3350 is about 37.7 g. In some embodiments, a non-colonic cleansing amount of PEG, e.g., PEG 3350, is about 33.9 g to about 41.5 g. In a specific embodiment, a non-colonic cleansing amount of PEG, e.g., PEG 3350 is about 40.2 g. In some embodiments, a non-colonic cleansing amount of PEG, e.g., PEG 3350, is about 36.2 g to about 44.2 g.

In some embodiments, a non-colonic cleansing amount of PEG, e.g., PEG 3350, is about 29.3 g, about 29.4 g, about 29.5 g, about 29.6 g, about 29.7 g, about 29.8 g, about 29.9 g, about 30.0 g, about 30.1 g, about 30.2 g, about 30.3 g, about 30.4 g, about 30.5 g, about 30.6 g, about 30.7 g, about 30.8 g, about 30.9 g, about 31.0 g, about 31.1 g, about 31.2 g, about 31.3 g, about 31.4 g, about 31.5 g, about 31.6 g, about 31.7 g, about 31.8 g, about 31.9 g, about 32.0 g, about 32.1 g, about 32.2 g, about 32.3 g, about 32.4 g, about 32.5 g, about 32.6 g, about 32.7 g, about 32.8 g, about 32.9 g, about 33.0 g, about 33.1 g, about 33.2 g, about 33.3 g, about 33.4 g, about 33.5 g, about 33.6 g, about 33.7 g, about 33.8 g, about 33.9 g, about 34.0 g, about 34.1 g, about 34.2 g, about 34.3 g, about 34.4 g, about 34.5 g, about 34.6 g, about 34.7 g, about 34.8 g, about 34.9 g, about 35.0 g, about 35.1 g, about 35.2 g, about 35.3 g, about 35.4 g, about 35.5 g, about 35.6 g, about 35.7 g, or about 35.8 g. In a specific embodiment, a non-colonic cleansing amount of PEG, e.g., PEG 3350 is about 32.5 g. In some embodiments, a non-colonic cleansing amount of PEG, e.g., PEG 3350, is about 29.3 g to about 35.8 g.

In some embodiments, compositions disclosed herein are formulated as aqueous solutions comprising about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, or about 5.5 wt % of PEG. In certain embodiments, compositions disclosed herein are formulated as aqueous solutions comprising about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, or about 5.5 wt % of PEG 3350. In a specific embodiment, compositions disclosed herein are formulated as aqueous solutions comprising about 5.0 wt % of PEG. In certain embodiments, compositions disclosed herein are formulated as aqueous solutions comprising about 4.5 wt % to about 5.5 wt % of PEG. In a specific embodiment, compositions disclosed herein are formulated as aqueous solutions comprising about 5.0 wt % of PEG 3350. In certain embodiments, compositions disclosed herein are formulated as aqueous solutions comprising about 4.5 wt % to about 5.5 wt % of PEG 3350.

In some embodiments, compositions disclosed herein are formulated as aqueous solutions comprising about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, or about 5.1 wt % of PEG. In some embodiments, compositions disclosed herein are formulated as aqueous solutions comprising about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, or about 5.1 wt % of PEG 3350. In a specific embodiment, compositions disclosed herein are formulated as aqueous solutions comprising about 4.6 wt % of PEG. In certain embodiments, compositions disclosed herein are formulated as aqueous solutions comprising about 4.2 wt % to about 5.1 wt % of PEG. In a specific embodiment, compositions disclosed herein are formulated as aqueous solutions comprising about 4.6 wt % of PEG 3350. In certain embodiments, compositions disclosed herein are formulated as aqueous solutions comprising about 4.2 wt % to about 5.1 wt % of PEG 3350.

In some embodiments, compositions disclosed herein comprise glucose. In some embodiments, compositions disclosed herein comprise about 19 g, about 20 g, about 21 g, about 22 g, about 23 g, about 24 g, about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, about 50 g, about 51 g, about 52 g, about 53 g, about 54 g, about 55 g, about 56 g, about 57 g, about 58 g, about 59 g, or about 60 g of glucose. In a specific embodiment, compositions disclosed herein comprise about 40 g of glucose. In certain embodiments, compositions disclosed herein comprise about 25 g to about 60 g of glucose, or about 25 g to about 50 g of glucose. In a specific embodiment, compositions disclosed herein comprise about 30 g of glucose. In certain embodiments, compositions disclosed herein comprise about 19 g to about 45 g of glucose, or about 19 g to about 38 g of glucose. In a specific embodiment, compositions disclosed herein comprise about 32 g of glucose. In certain embodiments, compositions disclosed herein comprise about 20 g to about 48 g of glucose, or about 20 g to about 40 g of glucose.

In some embodiments, compositions disclosed herein comprise about 25 g, about 26 g, about 27 g, about 28 g, about 29 g, about 30 g, or about 31 g of glucose. In a specific embodiment, compositions disclosed herein comprise about 28 g of glucose. In certain embodiments, compositions disclosed herein comprise about 25 g to about 31 g of glucose In some embodiments, compositions disclosed herein are formulated as aqueous solutions comprising about 2.5 wt %, about 2.6 wt %, about 2.7 wt %, about 2.8 wt %, about 2.9 wt %, about 3.0 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4.0 wt %, about 4.1 wt %, about 4.2 wt %, about 4.3 wt %, about 4.4 wt %, about 4.5 wt %, about 4.6 wt %, about 4.7 wt %, about 4.8 wt %, about 4.9 wt %, about 5.0 wt %, about 5.1 wt %, about 5.2 wt %, about 5.3 wt %, about 5.4 wt %, about 5.5 wt %, about 5.6 wt %, about 5.7 wt %, about 5.8 wt %, about 5.9 wt % or about 6.0 wt % of glucose. In a specific embodiment, compositions disclosed herein are formulated as aqueous solutions comprising about 4 wt % of glucose. In certain embodiments, compositions disclosed herein are formulated as aqueous solutions comprising about 2.5 wt % to about 6.0 wt % of glucose, or about 2.5 wt % to about 5.0 wt % of glucose.

In some embodiments, compositions disclosed herein are formulated as aqueous solutions comprising about 3.6 wt %, about 3.7 wt %, about 3.8 wt %, about 3.9 wt %, about 4.0 wt %, about 4.1 wt %, about 4.2 wt %, about 4.3 wt %, or about 4.4 wt % of glucose. In a specific embodiment, compositions disclosed herein are formulated as aqueous solutions comprising about 4 wt % of glucose. In certain embodiments, compositions disclosed herein are formulated as aqueous solutions comprising about 3.6 wt % to about 4.4 wt % of glucose.

In some embodiments, compositions disclosed herein comprise one or more electrolytes. In certain embodiments, the one or more electrolytes comprise sodium chloride (NaCl). In some embodiments, compositions disclosed herein comprise about 1.0 g, about 1.1 g, about 1.2 g, about 1.3 g, about 1.4 g, about 1.5 g, about 1.6 g, or about 1.7 of sodium chloride. In a specific embodiment, compositions disclosed herein comprise about 1.5 g of sodium chloride. In some embodiments, compositions disclosed herein comprise about 1.3 g to about 1.7 g of sodium chloride. In a specific embodiment, compositions disclosed herein comprise about 1.1 g of sodium chloride. In some embodiments, compositions disclosed herein comprise about 1.0 g to about 1.2 g of sodium chloride. In a specific embodiment, compositions disclosed herein comprise about 1.2 g of sodium chloride. In some embodiments, compositions disclosed herein comprise about 1.1 g to about 1.3 g of sodium chloride.

In some embodiments, compositions disclosed herein comprise about 0.9 g, about 1.0 g, or about 1.1 g of sodium chloride. In a specific embodiment, compositions disclosed herein comprise about 1.0 g of sodium chloride. In some embodiments, compositions disclosed herein comprise about 0.9 g to about 1.1 g of sodium chloride.

In some embodiments, compositions disclosed herein are formulated as aqueous solutions comprising about 0.13 wt %, about 0.14 wt %, about 0.15 wt %, about 0.16 wt %, about 0.17 wt % of sodium chloride. In a specific embodiment, compositions disclosed herein are formulated as aqueous solutions comprising about 0.15 wt % of sodium chloride. In some embodiments, compositions disclosed herein are formulated as aqueous solutions comprising about 0.13 wt % to about 0.17 wt % of sodium chloride.

In some embodiments, the one or more electrolytes comprise sodium sulfate ($Na_2SO_4$). In some embodiments, compositions disclosed herein comprise about 3.9 g, about 4.0 g, about 4.1 g, about 4.2 g, about 4.3 g, about 4.4 g, about 4.5 g, about 4.6 g, about 4.7 g, about 4.8 g, about 4.9 g, about 5.0 g, about 5.1 g, about 5.2 g, about 5.3 g, about 5.4 g, about 5.5 g, about 5.6 g, about 5.7 g, about 5.8 g, about 5.9 g, about 6.0 g, about 6.1 g, about 6.2 or about 6.3 g of sodium sulfate. In a specific embodiment, compositions disclosed herein comprise about 5.7 g of sodium sulfate. In some embodiments, compositions disclosed herein comprise about 5.1 g to about 6.3 g of sodium sulfate. In a specific embodiment, compositions disclosed herein comprise about 4.3 g of sodium sulfate. In some embodiments, compositions disclosed herein comprise about 3.9 g to about 4.7 g of sodium sulfate. In a specific embodiment, compositions disclosed herein comprise about 4.6 g of sodium sulfate. In some embodiments, compositions disclosed herein comprise about 4.1 g to about 5.1 g of sodium sulfate.

In some embodiments, compositions disclosed herein comprise about 3.6 g, about 3.7 g, about 3.8 g, about 3.9 g, about 4.0 g, about 4.1 g, about 4.2 g, about 4.3 g, or about 4.4 g of sodium sulfate. In a specific embodiment, compositions disclosed herein comprise about 4.0 g of sodium sulfate. In some embodiments, compositions disclosed herein comprise about 3.6 g to about 4.4 g of sodium sulfate.

In some embodiments, compositions disclosed herein are formulated as aqueous solutions comprising sodium sulfate. In some embodiments, the compositions disclosed herein are formulated as aqueous solutions comprising about 0.51 wt %, about 0.52 wt %, about 0.53 wt %, about 0.54 wt %, about 0.55 wt %, about 0.56 wt %, about 0.57 wt %, about 0.58 wt %, about 0.59 wt %, about 0.60 wt %, about 0.61 wt %, about 0.62 wt %, or about 0.63 wt % of sodium sulfate. In a specific embodiment, compositions disclosed herein are formulated as aqueous solutions comprising about 0.57 wt % of sodium sulfate. In some embodiments, compositions disclosed herein are formulated as aqueous solutions comprising about 0.51 wt % to about 0.63 wt % of sodium sulfate.

In some embodiments, the one or more electrolytes comprise sodium bicarbonate ($NaHCO_3$). In some embodiments, compositions disclosed herein comprise about 1.2 g, about 1.3 g, about 1.4 g, about 1.5 g, about 1.6 g, about 1.7 g, about 1.8 g, or about 1.9 g of sodium bicarbonate. In a specific embodiment, compositions disclosed herein comprise about 1.7 g of sodium bicarbonate. In some embodiments, compositions disclosed herein comprise about 1.5 g to about 1.9 g of sodium bicarbonate. In a specific embodiment, compositions disclosed herein comprise about 1.3 g of sodium bicarbonate. In some embodiments, compositions disclosed herein comprise about 1.2 g to about 1.4 g of sodium bicarbonate. In a specific embodiment, compositions disclosed herein comprise about 1.4 g of sodium bicarbonate. In some embodiments, compositions disclosed herein comprise about 1.3 g to about 1.5 g of sodium bicarbonate.

In some embodiments, compositions disclosed herein comprise about 1.1 g, about 1.2 g, or about 1.3 g of sodium bicarbonate. In a specific embodiment, compositions disclosed herein comprise about 1.2 g of sodium bicarbonate. In some embodiments, compositions disclosed herein comprise about 1.1 g to about 1.3 g of sodium bicarbonate.

In some embodiments, compositions disclosed herein are formulated as aqueous solutions comprising about 0.15 wt %, about 0.16 wt %, about 0.17 wt %, about 0.18 wt %, or about 0.19 wt % of sodium bicarbonate. In a specific embodiment, compositions disclosed herein are formulated as aqueous solutions comprising about 0.17 wt % of sodium bicarbonate. In some embodiments, compositions disclosed herein are formulated as aqueous solutions comprising about 0.15 wt % to about 0.19 wt % of sodium bicarbonate.

In some embodiments, compositions disclosed herein are formulated as aqueous solutions comprising about 0.16 wt %, about 0.17 wt %, about 0.18 wt %, or about 0.19 wt % of sodium bicarbonate. In a specific embodiment, compositions disclosed herein are formulated as aqueous solutions comprising about 0.17 wt % of sodium bicarbonate. In some embodiments, compositions disclosed herein are formulated as aqueous solutions comprising about 0.16 wt % to about 0.19 wt % of sodium bicarbonate.

In some embodiments, the one or more electrolytes comprise potassium chloride (KCl). In some embodiments, compositions disclosed herein comprise about 0.4 g, about 0.5 g, about 0.6 g, about 0.7 g or about 0.8 g of potassium chloride. In a specific embodiment, compositions disclosed herein comprise about 0.7 g of potassium chloride. In some embodiments, compositions disclosed herein comprise about 0.6 g to about 0.8 g of potassium chloride. In a specific embodiment, compositions disclosed herein comprise about 0.5 g of potassium chloride. In some embodiments, compositions disclosed herein comprise about 0.4 g to about 0.6 g of potassium chloride. In a specific embodiment, compositions disclosed herein comprise about 0.6 g of potassium chloride. In some embodiments, compositions disclosed herein comprise about 0.5 g to about 0.7 g of potassium chloride.

In some embodiments, compositions disclosed herein comprise about 0.4 g, about 0.5 g, or about 0.6 g of potassium chloride. In a specific embodiment, compositions disclosed herein comprise about 0.5 g of potassium chloride. In some embodiments, compositions disclosed herein comprise about 0.4 g to about 0.6 g of potassium chloride.

In some embodiments, compositions disclosed herein are formulated as aqueous solutions comprising about 0.06 wt %, about 0.07 wt %, or about 0.08 wt % of potassium chloride. In a specific embodiment, compositions disclosed herein are formulated as aqueous solutions comprising about 0.07 wt % of potassium chloride. In some embodiments, compositions disclosed herein are formulated as aqueous solutions comprising about 0.06 wt % to about 0.08 wt % of potassium chloride.

In some embodiments, compositions disclosed herein are formulated as aqueous solutions comprising about 0.06 wt %, about 0.07 wt %, about 0.08 wt %, or about 0.09% wt of potassium chloride. In a specific embodiment, compositions disclosed herein are formulated as aqueous solutions comprising about 0.07 wt % of potassium chloride. In some embodiments, compositions disclosed herein are formulated as aqueous solutions comprising about 0.06 wt % to about 0.09 wt % of potassium chloride.

In some embodiments, the compositions disclosed herein are formulated into any suitable dosage form, including but not limited to solutions, dispersions, self-emulsifying dispersions, solid solutions, liposomal dispersions, liquids, gels, syrups, elixirs, lyophilized formulations, powders, or multiparticulate formulations. Such formulations are optionally manufactured in a conventional manner, such as, by way of example only, conventional mixing, dissolving, emulsifying, and the like. In some embodiments, compositions disclosed herein are formulated as a powder for reconstitution. In some embodiments, compositions disclosed herein are formulated as an aqueous solution.

In certain embodiments, compositions disclosed herein are formulated as a solution, e.g., an aqueous solution. In some embodiments, compositions disclosed herein are formulated as a solution, e.g., an aqueous solution, having a volume of about 500 mL, about 510 mL, about 520 mL, about 530 mL, about 540 mL, about 550 mL, about 560 mL, about 570 mL, about 580 mL, about 590 mL, about 600 mL, about 610 mL, about 620 mL, about 630 mL, about 640 mL, about 650 mL, about 660 mL, about 670 mL, about 680 mL, about 690 mL, about 700 mL, about 710 mL, about 720 mL, about 730 mL, about 740 mL, about 750 mL, about 760 mL, about 770 mL, about 780 mL, about 790 mL, about 800 mL, about 810 mL, about 820 mL, about 830 mL, about 840 mL, about 850 mL, about 860 mL, about 870 mL, about 880 mL, about 890 mL, about 900 mL, about 910 mL, about 920 mL, about 930 mL, about 940 mL, about 950 mL, about 960 mL, about 970 mL, about 980 mL, about 990 mL, or about 1000 mL. In some embodiments, compositions disclosed herein are formulated as a solution, e.g., an aqueous solution, having a volume of about 500 mL to about 1000 mL. In some embodiments, compositions disclosed herein are formulated as a solution, e.g., an aqueous solution, having a volume of about 750 mL to about 1000 mL.

In some embodiments, compositions disclosed herein are formulated as a solution, e.g., an aqueous solution, having a volume of about 630 mL, about 640 mL, about 650 mL, about 660 mL, about 670 mL, about 680 mL, about 690 mL, about 700 mL, about 710 mL, about 720 mL, about 730 mL, about 740 mL, about 750 mL, about 760 mL, or about 770 mL. In a specific embodiment, compositions disclosed herein are formulated as a solution, e.g., an aqueous solution, having a volume of about 700 mL. In some embodiments, compositions disclosed herein are formulated as a solution, e.g., an aqueous solution, having a volume of about 630 mL to about 770 mL.

In some embodiments, compositions disclosed herein comprise about 7.0 g to about 8.6 g of tranexamic acid and about 25 g to about 60 g of glucose. In some embodiments, compositions disclosed herein comprise about 7.0 g to about 8.6 g of tranexamic acid and about 25 g to about 50 g of glucose. In certain specific embodiments, compositions disclosed herein comprise about 7.8 g of tranexamic acid and about 19 g, about 20 g, about 21 g, about 22 g, about 23 g, about 24 g, about 25 g, about 26 g, about 27 g, about 28 g, about 29 g, about 30 g, about 31 g, about 32 g, about 33 g, about 34 g, about 35 g, about 36 g, about 37 g, about 38 g, about 39 g, about 40 g, about 41 g, about 42 g, about 43 g, about 44 g, about 45 g, about 46 g, about 47 g, about 48 g, about 49 g, about 50 g, about 51 g, about 52 g, about 53 g, about 54 g, about 55 g, about 56 g, about 57 g, about 58 g, about 59 g, or about 60 g of glucose. In a specific embodiment, compositions disclosed herein comprise about 7.8 g of tranexamic acid and about 40 g of glucose.

In some embodiments, compositions disclosed herein comprise about 6.8 g to about 8.3 g of tranexamic acid and about 25 g to about 31 g of glucose. In certain specific embodiments, compositions disclosed herein comprise about 7.5 g of tranexamic acid and about 25 g, about 26 g, about 27 g, about 28 g, about 29 g, about 30 g, or about 31 g of glucose. In a specific embodiment, compositions disclosed herein comprise about 7.5 g of tranexamic acid and about 28 g of glucose.

In some embodiments, compositions disclosed herein comprise about 7.0 g to about 8.6 g of tranexamic acid and about 45.2 g to about 55.3 g of PEG 3350. In some embodiments, compositions disclosed herein comprise about 7.0 g to about 8.6 g of tranexamic acid and about 33.9 g to about 41.5 g of PEG 3350. In some embodiments, compositions disclosed herein comprise about 7.0 g to about 8.6 g of tranexamic acid and about 36.2 g to about 44.2 g of PEG 3350. In certain specific embodiments, compositions disclosed herein comprise about 7.8 g of tranexamic acid and about 33.9 g, about 34.0 g, about 34.1 g, about 34.2 g, about 34.3 g, about 34.4 g, about 34.5 g, about 34.6 g, about 34.7 g, about 34.8 g, about 34.9 g, about 35.0 g, about 35.1 g, about 35.2 g, about 35.3 g, about 35.4 g, about 35.5 g, about 35.6 g, about 35.7 g, about 35.8 g, about 35.9 g, about 36.0 g, about 36.1 g, about 36.2 g, about 36.3 g, about 36.4 g, about 36.5 g, about 36.6 g, about 36.7 g, about 36.8 g, about 36.9 g, about 37.0 g, about 37.1 g, about 37.2 g, about 37.3 g, about 37.4 g, about 37.5 g, about 37.6 g, about 37.7 g, about 37.8 g, about 37.9 g, about 38.0 g, about 38.1 g, about 38.2 g, about 38.3 g, about 38.4 g, about 38.5 g, about 38.6 g, about 38.7 g, about 38.8 g, about 38.9 g, about 39.0 g, about 39.1 g, about 39.2 g, about 39.3 g, about 39.4 g, about 39.5 g, about 39.6 g, about 39.7 g, about 39.8 g, about 39.9 g, about 40.0 g, about 40.1 g, about 40.2 g, about 40.3 g, about 40.4 g, about 40.5 g, about 40.6 g, about 40.7 g, about 40.8 g, about 40.9 g, about 41.0 g, about 41.1 g, about 41.2, about 41.3 g, about 41.4 g, about 41.5 g, about 41.6 g, about 41.7 g, about 41.8 g, about 41.9 g, about 42.0 g, about 42.1 g, about 42.2 g, about 42.3 g, about 42.4 g, about 42.5 g, about 42.6 g, about 42.7 g, about 42.8 g, about 42.9 g, about 43.0 g, about 43.1 g, about 43.2 g, about 43.3 g, about 43.4 g, about 43.5 g, about 43.6 g, about 43.7 g, about 43.8 g, about 43.9 g, about 44.0 g, about 44.1 g, about 44.2 g, about 44.3 g, about 44.4 g, about 44.5 g, about 44.6 g, about 44.7 g, about 44.8 g, about 44.9 g, about 45.0 g, about 45.1 g, about 45.2 g, about 45.3 g, about 45.4 g, about 45.5 g, about 45.6 g, about 45.7 g, about 45.8 g, about 45.9 g, about 46.0 g, about 46.1 g, about 46.2 g, about 46.3 g, about 46.4 g, about 46.5 g, about 46.6 g, about 46.7 g, about 46.8 g, about 46.9 g, about 47.0 g, about 47.1 g, about 47.2 g, about 47.3 g, about 47.4 g, about 47.5 g, about 47.6 g, about 47.7 g, about 47.8 g, about 47.9 g, about 48.0 g, about 48.1 g, about 48.2 g, about 48.3 g, about 48.4 g, about 48.5 g, about 48.6 g, about 48.7 g, about 48.8 g, about 48.9 g, about 49.0 g, about 49.1 g, about 49.2 g, about 49.3 g, about 49.4 g, about 49.5 g, about 49.6 g, about 49.7 g, about 49.8 g, about 49.9 g, about 50.0 g, about 50.1 g, about 50.2 g, about 50.3 g, about 50.4 g, about 50.5 g, about 50.6 g, about 50.7 g, about 50.8 g, about 50.9 g, about 51.0 g, about 51.1 g, about 51.2 g, about 51.3 g, about 51.4 g, about 51.5 g, about 51.6 g, about 51.7 g, about 51.8 g, about 51.9 g, about 52.0 g, about 52.1 g, about 52.2 g, about 52.3 g, about 52.4 g, about 52.5 g, about 52.6 g, about 52.7 g, about 52.8 g, about 52.9 g, about 53.0 g, about 53.1 g, about 53.2 g, about 53.3 g, about 53.4 g, about 53.5 g, about 53.6 g, about 53.7 g, about 53.8 g, about 53.9 g, about 54.0 g, about 54.1 g, about 54.2 g, about 54.3 g, about 54.4 g, about 54.5 g, about 54.6 g, about 54.7 g, about 54.8 g, about 54.9 g, about 55.0 g, about 55.1 g, about 55.2 g, or about 55.3 g of PEG 3350. In a specific embodiment, compositions disclosed herein comprise about 7.8 g of tranexamic acid and about 59.0 g of PEG 3350. In a specific embodiment, compositions disclosed herein comprise about 7.8 g of tranexamic acid and about 40.2 g of PEG 3350. In a specific embodiment, compositions disclosed herein comprise about 7.8 g of tranexamic acid and about 37.7 g of PEG 3350.

In some embodiments, compositions disclosed herein comprise about 6.8 g to about 8.3 g of tranexamic acid and about 29.3 g to about 35.8 g of PEG 3350. In certain specific embodiments, compositions disclosed herein comprise about 7.5 g of tranexamic acid and about 29.3 g, about 29.4 g, about 29.5 g, about 29.6 g, about 29.7 g, about 29.8 g, about 29.9 g, about 30.0 g, about 30.1 g, about 30.2 g, about 30.3 g, about 30.4 g, about 30.5 g, about 30.6 g, about 30.7 g, about 30.8 g, about 30.9 g, about 31.0 g, about 31.1 g, about 31.2 g, about 31.3 g, about 31.4 g, about 31.5 g, about 31.6 g, about 31.7 g, about 31.8 g, about 31.9 g, about 32.0 g, about 32.1 g, about 32.2 g, about 32.3 g, about 32.4 g, about 32.5 g, about 32.6 g, about 32.7 g, about 32.8 g, about 32.9 g, about 33.0 g, about 33.1 g, about 33.2 g, about 33.3 g, about 33.4 g, about 33.5 g, about 33.6 g, about 33.7 g, about 33.8 g, about 33.9 g, about 34.0 g, about 34.1 g, about 34.2 g, about 34.3 g, about 34.4 g, about 34.5 g, about 34.6 g, about 34.7 g, about 34.8 g, about 34.9 g, about 35.0 g, about 35.1 g, about 35.2 g, about 35.3 g, about 35.4 g, about 35.5 g, about 35.6 g, about 35.7 g, or about 35.8 g of PEG 3350. In a specific embodiment, compositions disclosed herein comprise about 7.5 g of tranexamic acid and about 32.5 g of PEG 3350.

In some embodiments, compositions disclosed herein are formulated as aqueous solutions comprising about 7.0 g to about 8.6 g of tranexamic acid, about 4.5 wt % to about 5.5 wt % of PEG 3350, about 2.5 wt % to about 6 wt % of glucose, about 0.51 wt % to about 0.63 wt % of sodium sulfate, about 0.15 wt % to about 0.19 wt % of sodium bicarbonate, about 0.13 wt % to about 0.17 wt % of sodium chloride, and about 0.06 wt % to about 0.08 wt % of potassium chloride. In some embodiments, compositions disclosed herein are formulated as aqueous solutions comprising about 7.0 g to about 8.6 g of tranexamic acid, about 4.5 wt % to about 5.5 wt % of PEG 3350, about 2.5 wt % to about 5 wt % of glucose, about 0.51 wt % to about 0.63 wt % of sodium sulfate, about 0.15 wt % to about 0.19 wt % of sodium bicarbonate, about 0.13 wt % to about 0.17 wt % of sodium chloride, and about 0.06 wt % to about 0.08 wt % of potassium chloride. In a specific embodiment, compositions disclosed herein are formulated as aqueous solutions comprising about 7.8 g of tranexamic acid, about 5.0 wt % of PEG 3350, about 4 wt % of glucose, about 0.57 wt % of sodium sulfate, about 0.17 wt % of sodium bicarbonate, about 0.15 wt % of sodium chloride, and about 0.07 wt % of potassium chloride.

In some embodiments, compositions disclosed herein are formulated as aqueous solutions comprising about 6.8 g to about 8.3 g of tranexamic acid, about 4.2 wt % to about 5.1 wt % of PEG 3350, about 3.6 wt % to about 4.4 wt % of glucose, about 0.51 wt % to about 0.63 wt % of sodium sulfate, about 0.16 wt % to about 0.19 wt % of sodium bicarbonate, about 0.13 wt % to about 0.17 wt % of sodium chloride, and about 0.06 wt % to about 0.09 wt % of potassium chloride. In a specific embodiment, compositions disclosed herein are formulated as aqueous solutions comprising about 7.5 g of tranexamic acid, about 4.6 wt % of PEG 3350, about 4 wt % of glucose, about 0.57 wt % of sodium sulfate, about 0.17 wt % of sodium bicarbonate, about 0.15 wt % of sodium chloride, and about 0.07 wt % of potassium chloride.

In some embodiments, the compositions disclosed herein are formulated with one or more inactive ingredients or pharmaceutical excipients that provide suitable properties of the formulation. Such inactive ingredients include but are not limited to antioxidants, carriers, viscosity modulating agents, diluents, flavoring agents, preservatives, solubilizers, stabilizers, suspending agents, and surfactants. Any suitable amounts of such inactive ingredients are determined according to the particular properties desired.

Methods of Treatment

In some embodiments, the compositions disclosed herein are administered for the treatment of shock, autodigestion, multi-organ failure, ischemia, or hypoperfusion. In certain specific embodiments, compositions disclosed herein are administered for the treatment of cardiogenic shock, hemorrhagic shock, or septic shock. In some embodiments, ischemia is intestinal ischemia. In some embodiments, compositions disclosed herein are administered for the treatment of septic shock associated with or caused by sepsis. In some embodiments, compositions disclosed herein are administered for the treatment of cardiovascular shock associated with or caused by cardiovascular surgery, myocardial infarction, arrhythmia, or mechanical complications. In some embodiments, a mechanical complication is a cardiovascular mechanical complication. In some embodiments, compositions disclosed herein are administered for the treatment of cardiovascular shock associated with or caused by myocardial infarction or mechanical complications. In some embodiments, compositions disclosed herein are administered for the treatment of hemorrhagic or hypovolemic shock associated with or caused by trauma. In some embodiments, compositions disclosed herein may be administered for the treatment of hemorrhagic or hypovolemic shock associated with or caused by Ebola Virus Disease or other hemorrhagic virus. In some embodiments, compositions disclosed herein are administered for the treatment of intestinal ischemia or hypoperfusion that result in shock. In some embodiments, compositions disclosed herein may be administered for the treatment of Inflammatory Bowel Disease or Crohn's Disease, or complications arising from Inflammatory Bowel Disease or Crohn's Disease. In some embodiments, compositions disclosed herein may be administered for the treatment of *Clostridium difficile* colitis, or complications that arise from *Clostridium difficile* colitis.

In some embodiments, the compositions disclosed herein are administered to a subject, e.g., a human, by multiple administration routes, either alone or concurrently, including but not limited to oral, nasogastric, orogastric, nasojejunal, orojejunal, nasoduodenal, or percutaneous endoscopic gastrostomy administration or other enteral routes. In some embodiments, compositions disclosed herein are administered directly to the gastrointestinal tract. In some embodiments, compositions disclosed herein are administered to the stomach. In some embodiments, compositions disclosed herein are administered to the small intestine. In certain embodiments, compositions disclosed herein are administered via a nasogastic, orogastic, nasojejunal, orojejunal, nasoduodenal, or percutaneous endoscopic gastrostomy tube or catheter. In some embodiments, compositions disclosed herein are delivered orally or by direct injection. In some embodiments of the methods disclosed herein, compositions are administered by a single route of administration. In some embodiments of the methods disclosed herein, compositions are administered by multiple routes of administration.

Kits

In some embodiments, the components of the compositions disclosed herein are provided in kits wherein one or more of the components are contained in separate packages or containers along with instructions to combine the components in a single composition. In some embodiments, a kit comprises instructions to reconstitute the components in a liquid carrier, such as water, to produce a liquid, e.g., aqueous, formulation comprising the components. In some instances, the components of the compositions disclosed herein are provided in a single package or container with instructions to reconstitute them in a liquid carrier, such as water, to produce a liquid, e.g., aqueous, formulation. In some embodiments, the components of the compositions disclosed herein are provided in kits wherein one or more of the components are contained in separate packages or containers, and wherein a liquid carrier, such as water, is also provided in a separate package or container in the kit, along with instructions to combine the components and liquid carrier in a single composition to produce a liquid, e.g., aqueous, formulation. In some embodiments, a kit comprises instructions to administer a composition or formulation disclosed herein orally or via a nasogastic, orogastic, nasojejunal, orojejunal, nasoduodenal, or percutaneous endoscopic gastrostomy tube or catheter to a subject, e.g., a human, to treat shock, autodigestion, multi-organ failure, ischemia, or hypoperfusion.

In certain specific embodiments, a kit comprises tranexamic acid and glucose packaged in separate containers. In some embodiments, a kit comprises tranexamic acid, polyethylene glycol, and one or more electrolytes in a first container and glucose in a second container. In some embodiments, a kit comprises tranexamic acid and polyethylene glycol in a first container and glucose and one or more electrolytes in a second container. In some embodiments, a kit comprises tranexamic acid and electrolytes in a first container and glucose and polyethylene glycol in a second container. In some embodiments, a kit comprises tranexamic acid in a first container and glucose, polyethylene glycol, and electrolytes in a second container. In some instances, the containers are made of any suitable packaging material and in any form suitable for the distribution of pharmaceutical products.

In some embodiments, disclosed herein is a kit comprising: the components tranexamic acid, PEG, glucose, and one or more electrolytes, wherein at least one of the components tranexamic acid, PEG, glucose, and one or more electrolytes is in a separate container from at least one of the other components tranexamic acid, PEG, glucose, and one or more electrolytes; and instructions to combine the components tranexamic acid, PEG, glucose, and one or more electrolytes in a single composition. In some embodiments, a kit comprises tranexamic acid, PEG, and one or more electrolytes are in a first container, and glucose in a second container. In some embodiments, a kit comprises instructions to combine the tranexamic acid, PEG, one or more electrolytes, and glucose, and reconstitute them in water. In some embodiments, a kit comprises a first container comprising about 7.8 g of tranexamic acid, about 50.3 g of PEG 3350, about 5.7 g of sodium sulfate, about 1.7 g of sodium bicarbonate, about 1.5 g of sodium chloride, and about 0.7 g of potassium chloride, and a second container comprising about 40 g of glucose. In some embodiments, a kit comprises a first container comprising about 7.8 g of tranexamic acid, about 50.3 g of PEG 3350, about 5.7 g of sodium sulfate, about 1.7 g of sodium bicarbonate, about 1.5 g of sodium chloride, and about 0.7 g of potassium chloride, a second container comprising about 40 g of glucose, and instructions to reconstitute the tranexamic acid, PEG, glucose, and one or more electrolytes with water to 1000 mL. In some embodiments, a kit comprises a first container comprising about 7.5 g of tranexamic acid, about 32.5 g of PEG 3350, about 4.0 g of sodium sulfate, about 1.2 g of sodium bicarbonate, about 1.0 g of sodium chloride, and about 0.5 g of potassium chloride, and a second container comprising about 28 g of glucose. In some embodiments, a kit comprises a first container comprising about 7.5 g of tranexamic acid, about 32.5 g of PEG 3350, about 4.0 g of sodium sulfate, about 1.2 g of sodium bicarbonate, about 1.0 g of sodium chloride, and about 0.5 g of potassium chloride, a second container comprising about 28 g of glucose, and instructions to reconstitute the tranexamic acid, PEG, glucose, and one or more electrolytes with water to 700 mL. In some embodiments, a kit comprises instructions to administer the combined components orally or via a nasogastric, orogastric, nasojejunal, orojejunal, nasoduodenal, or percutaneous endoscopic gastrostomy tube or catheter.

Testing

In some embodiments, the compositions disclosed herein are tested in animal models that are indicative of efficacy in the treatment of shock, autodigestion, multi-organ failure, trauma, sepsis, and ischemia. Such animal models include but are not limited to the minipig hemorrhagic shock model, rat hemorrhagic shock, rat superior mesentery artery occlusion shock, rodent peritonitis shock by placement of cecal material into the peritoneum, rodent endotoxin shock models, and rodent models of bacterial sepsis established through a *Pseudomonas* infection.

EXAMPLES

Example 1

Exemplary Compositions

Exemplary compositions are described in Tables 1 and 2. In some embodiments, the compositions according to the instant disclosure are prepared as a dry powder formulation and reconstituted as shown. Table 1 shows a composition for reconstitution in water to 1000 mL. Table 2 shows a composition for reconstitution in water to 700 mL. In some instances, upon reconstitution, compositions are administered to a patient in need thereof, e.g., orally or directly to the gastrointestinal tract via a nasogastric, orogastric, nasojejunal, orojejunal, nasoduodenal, or percutaneous endoscopic gastrostomy tube or catheter.

TABLE 1

| Component | Amount (g) for 1000 mL solution | Concentration (wt %) in 1000 mL aqueous solution |
|---|---|---|
| Tranexamic acid | 7.8 ± 10% | 0.78 ± 10% |
| PEG 3350 | 50.3 ± 10% | 5.03 ± 10% |
| Sodium Sulfate | 5.7 ± 10% | 0.57 ± 10% |
| Sodium Bicarbonate | 1.7 ± 10% | 0.17 ± 10% |
| Sodium Chloride | 1.5 ± 10% | 0.15 ± 10% |
| Potassium Chloride | 0.7 ± 10% | 0.07 ± 10% |
| Glucose | 40 ± 10% | 4.0 ± 10% |

TABLE 2

| Component | Amount (g) for 700 mL solution | Concentration (wt %) in 700 mL aqueous solution |
|---|---|---|
| Tranexamic acid | 7.5 ± 10% | 1.1 ± 10% |
| PEG 3350 | 32.5 ± 10% | 4.6 ± 10% |
| Sodium Sulfate | 4.0 ± 10% | 0.57 ± 10% |
| Sodium Bicarbonate | 1.2 ± 10% | 0.17 ± 10% |
| Sodium Chloride | 1.0 ± 10% | 0.15 ± 10% |
| Potassium Chloride | 0.5 ± 10% | 0.07 ± 10% |
| Glucose | 28 ± 10% | 4.0 ± 10% |

Example 2

Superior Mesentery Artery Occlusion (SMAO) Shock Studies with Formulations Administered Via Oral Gavage The SMAO model was used to assess the ability of a representative composition comprising PEG 3350 (Representative Formulation 1) and a comparative composition without PEG 3350 (Comparative Formulation 1) to preserve the structural integrity of the gastrointestinal tract under ischemic conditions when administered by oral gavage.

Formulation Preparation

The materials used to prepare the formulations and their sources are shown in Table 3. All materials used were USP grade. As shown in Table 3, Representative Formulation 1 comprises tranexamic acid, electrolytes, PEG 3350, and glucose, and Comparative Formulation 1 comprises tranexamic acid, electrolytes, and glucose.

TABLE 3

| Component | Representative Formulation 1 | Comparative Formulation 1 | Source |
|---|---|---|---|
| Tranexamic acid | 0.043 g | 0.043 g | Daiichi Sankyo |
| PEG 3350 | 0.287 g | 0.0 g | OTC clinical grade Miralax |
| Sodium Sulfate (Anhydrous) | 0.033 g | 0.033 g | Sigma-Aldrich |
| Sodium Bicarbonate | 0.010 g | 0.010 g | Sigma-Aldrich |
| Sodium Chloride | 0.009 g | 0.009 g | Sigma-Aldrich |
| Potassium Chloride | 0.004 g | 0.004 g | Sigma-Aldrich |
| Glucose | 0.229 g | 0.229 g | Sigma-Aldrich |

TABLE 3-continued

| Component | Representative Formulation 1 | Comparative Formulation 1 | Source |
|---|---|---|---|
| Water | 3.629 g | 3.629 g | Sterile water for injection |
| Total Solution | 4.000 mL | 4.000 mL | |

Rats and Diet

Male WISTAR rats with a weight of 360-400 grams were purchased from Charles River Laboratories, located in Wilmington, Mass. All rats were maintained on a 2018 Teklad Global 18% Protein Rodent Diet (Harlan, San Diego, Calif., USA) and water throughout the study period.

Formulation Administration

Food was removed from the cage the evening prior to surgery. Rats had ad lib access to drinking water while in the home cage the evening prior to surgery. During administration of the formulations, rats were restrained and given 4 mL of Representative Formulation 1 or Comparative Formulation 1 by oral gavage. After administration of the test formulations, rats were returned to their home cage and given ad lib access to water. After a 3 hour period, the rats were prepared to undergo experimentally induced shock.

Anesthesia and Preoperative Preparation

Animals were anesthetized with ketamine/xylazine (75/4 mg/kg, I.M.). Supplemental anesthesia (ketamine/xylazine 10% initial dose, I.M.) was administered as indicated following response to tail/toe pinch. Anesthesia was maintained throughout the experimental shock period.

Rats were secured in a supine position to a temperature controlled (water circulating heat pump) operating table. The animals were maintained at 37° C. throughout the procedures.

All surgical procedures were performed using aseptic techniques. Sterile drapes, heat sterilized instruments, and surgical apparel (gown, face mask, and gloves) were used. The surgical sites on the abdomen and left groin were shaved and cleaned with betadine followed by 70% alcohol.

SMAO Procedures

Following anesthetization, the superior mesentery artery was located and tied off (occluded) to prevent blood flow to the intestine and initiate a 30 minute shock/hypoperfusion period. The surgical site was covered with moistened sterile gauze during the entire SMAO shock period. After the 30 minute period, the SMAO was untied (occlusion removed). Perfusion was resumed for a period of 2 hours, followed by sacrifice of the animals.

Necropsy and Histological Processing

The intestines were then harvested by tying off both ends, injecting a 10% neutral buffered formalin solution with a 30 gauge needle, and storing the intestine in a jar filled with 10% neutral buffered formalin.

Following at least 24 hours of incubation in formalin, an approximate 5 cm by 5 cm section of the ileum (at approximately ⅝ the length of the small intestine) was excised for structural analysis. The tissue sample was adhered to a cardboard backing and mounted for sectioning. Intestinal cross sections of 15-20 microns thickness were created on a Vibratome Series 3000 sectioning system. Free floating sections were washed overnight in water to remove formalin. Sections were then free floating stained with Alcian blue (pH 2.5) (Diagnostic BioSystems, Catalog No. KT 003) and mounted on slides for analysis.

Tissue Analysis

A Leitz Wetzlar Dialux 20 microscope (Wetzlar, West Germany) and 20× objective was used to image tissue sections. Still images of the tissue were captured with a Spot Insight Gigabit Camera, Model No. 35.2, Diagnostic Instruments, Inc. (Sterling Heights, Mich.) and included software. Images were stored as TIFF files with no compression used. Images were loaded into Photoshop Elements 13 and enhanced to sharpen the contours of the villi. To quantify the extent of damage to the villi, villi were classified as damaged when either of the following criteria was met:
1) Villi tips were broken away or structural damage to any portion of the villi; or
2) Goblet cells (normally stained blue) were practically non-existent (≤3 goblet cells with no stain) from the base to the villi tip The Photoshop Text tool was used to place an n (for no damage) or a d (for damage) in proximity to each individual villi for each tissue cross section. Where a determination of damage was inconclusive, the villi were excluded from the analysis. These inconclusive villi were less than 5% of the total villi analyzed. An image demonstrating the identification methodology is in FIG. 1, which shows a cross section of the small intestine from a rat treated with an enteral formulation. Healthy villi are marked with n and damaged villi are marked with d.

Results

Figure 2A:
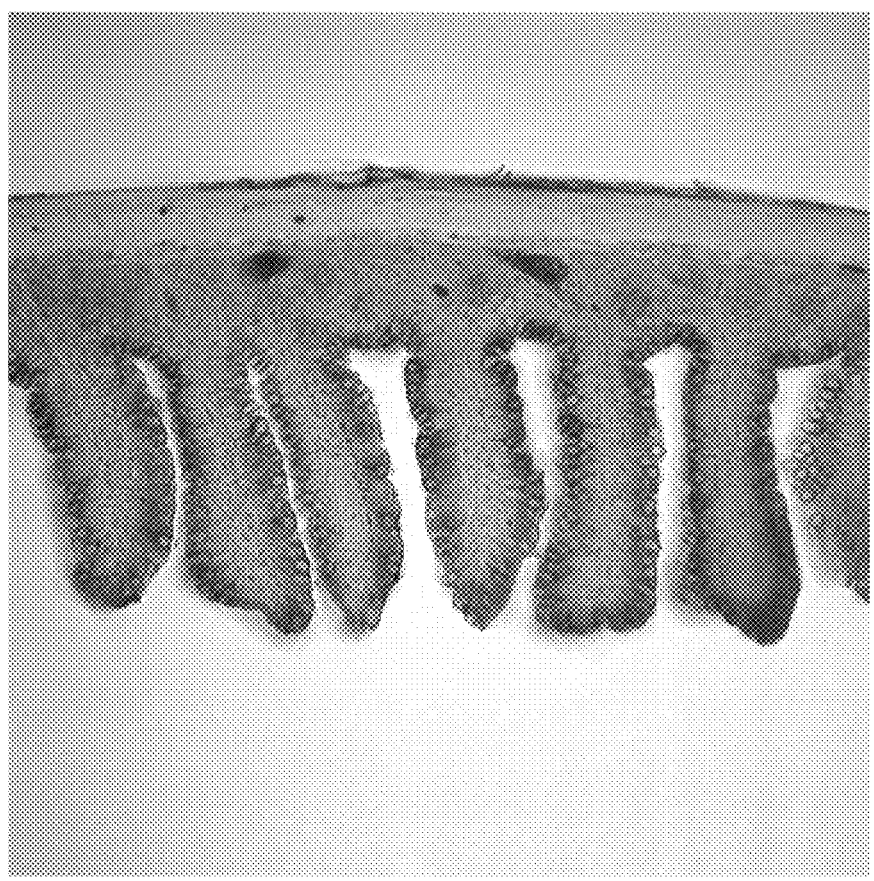
FIGS. 2A and 2B show the cross sections of the small intestines of rats following treatment with Representative Formulation 1 and Comparative Formulation 1, respectively.
Figure 2B:
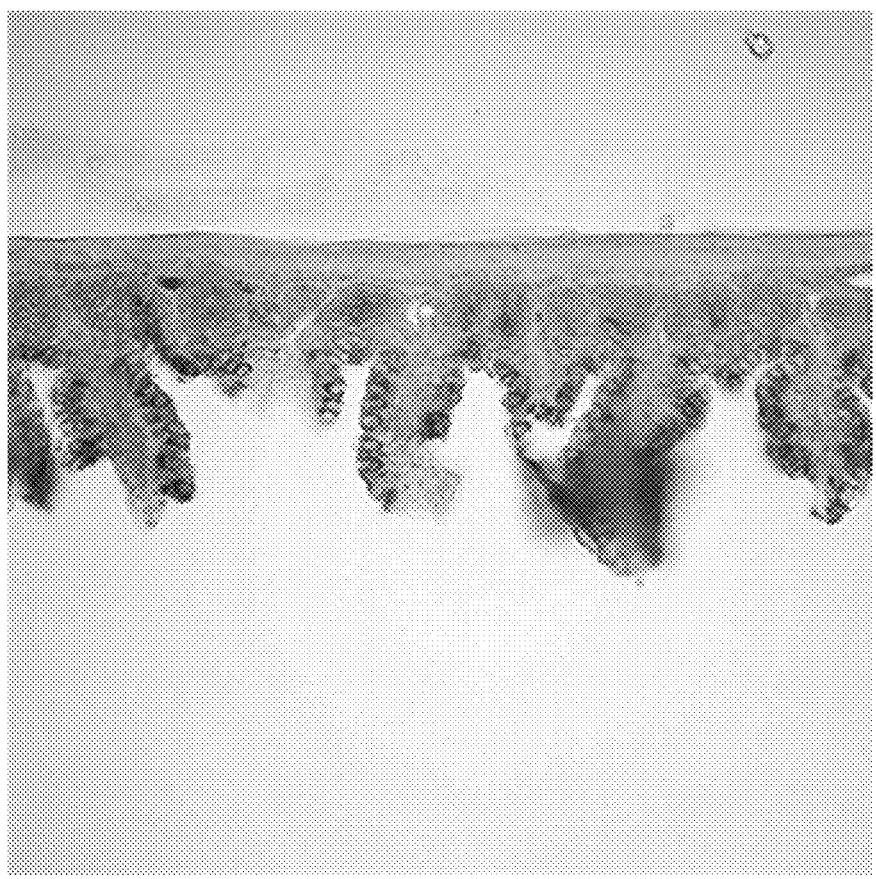

A total of eight rats were tested. Four received Representative Formulation 1 by oral gavage, and four rats received Comparative Formulation 1 by oral gavage. Representative micrographs of the villi after administration of the formulations and shock induction are shown in FIGS. 2A and 2B. FIG. 2A shows a cross section of the small intestine of a rat treated with Representative Formulation 1. The villi in FIG. 2A appear healthy and structurally intact as the entire length of the villi are visible and completely covered in goblet cells. FIG. 2B shows a cross section of the small intestine of a rat treated with Comparative Formulation 1. The villi in FIG. 2B appear to be structurally damaged with missing villi tips and atypical goblet cell staining.

Figure 3:
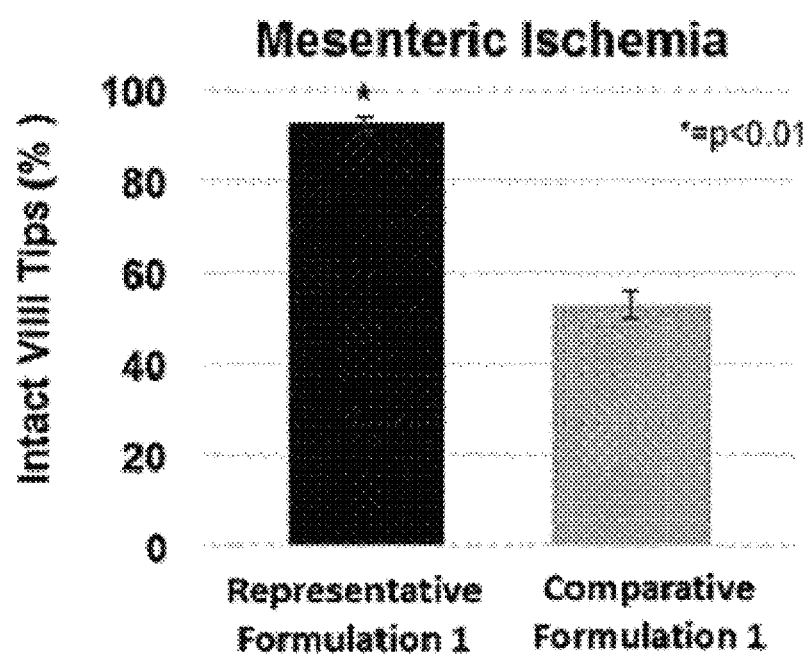
FIG. 3 illustrates the percentage of villi that were structurally intact with intact epithelial lining in all rats treated in Example 2. Representative Formulation 1 preserved on average 92.6% of villi, while Comparative Formulation 1 preserved on average 52.8% of the villi. Data are averages±SEM; n=4 rats in each group; *=$p<0.01$ compared to respective treated group, ANOVA.

Quantification of villi that were structurally intact after administration of the formulations and shock induction are shown in Tables 4 and 5 and FIG. 3. Table 4 shows the individual rat data for the quantification of the structurally intact villi. Table 5 summarizes the total intact villi and damaged villi observed after administration of the formulations and shock induction. FIG. 3 shows the mean percentage of villi intact per rat after administration of the formulations and shock induction. 92.6% of villi were intact across all rats that received Representative Formulation 1, whereas only 52.8% of the villi were intact across all rats that received Comparative Formulation 1. These results are consistent with the mean values calculated from the total villi observed in Table 5.

TABLE 4

| Rats Treated with Representative Formulation 1 | % Intact Villi | Rats Treated with Comparative Formulation 1 | % Intact Villi |
|---|---|---|---|
| Rat #11 | 90.9% | Rat #12 | 50.9% |
| Rat #13 | 90.2% | Rat #15 | 48.9% |
| Rat #14 | 91.3% | Rat #16 | 48.8% |
| Rat #18 | 97.9% | Rat #17 | 62.5% |
| Mean | 92.6% | Mean | 52.8% |
| SEM (+/−) | 1.8% | SEM (+/−) | 3.3% |

TABLE 5

| | Rats Treated with Representative Formulation 1 | Rats Treated with Comparative Formulation 1 |
|---|---|---|
| Number of Intact Villi | 176 | 94 |
| Number of Damaged Villi | 14 | 85 |
| Total Villi | 190 | 179 |
| % Intact | 92.6% | 52.5% |

Example 3

SMAO Shock Studies with Formulations Administered Via Direct Enteral Injection

The SMAO model was used to assess the ability of a representative composition comprising glucose (Representative Formulation 2) and a comparative composition without glucose (Comparative Formulation 2) to preserve the structural integrity of the gastrointestinal tract under ischemic conditions when administered by direct enteral injection.

Formulation Preparation

The materials used to prepare the formulations and their sources are shown in Table 6. All materials used were USP grade. As shown in Table 6, the Representative Formulation 2 comprises tranexamic acid, electrolytes, PEG 3350, and glucose, and Comparative Formulation 2 comprises tranexamic acid, electrolytes, and PEG 3350.

TABLE 6

| Component | Representative Formulation 2 | Comparative Formulation 2 | Source |
|---|---|---|---|
| Tranexamic acid | 0.182 g | 0.182 g | Daiichi Sankyo |
| PEG 3350 | 1.222 g | 1.222 g | OTC clinical grade Miralax |
| Sodium Sulfate (Anhydrous) | 0.138 g | 0.138 g | Sigma-Aldrich |
| Sodium Bicarbonate | 0.041 g | 0.041 g | Sigma-Aldrich |
| Sodium Chloride | 0.036 g | 0.036 g | Sigma-Aldrich |
| Potassium Chloride | 0.017 g | 0.017 g | Sigma-Aldrich |
| Glucose | 0.971 g | 0.0 g | Sigma-Aldrich |
| Water | 15.421 g | 15.421 g | Sterile water for injection |
| Total Solution | 17.000 mL | 17.000 mL | |

Rats and Diet

Male WISTAR rats with a weight of 360-400 grams were purchased from Charles River Laboratories, located in Wilmington, Mass. All rats were maintained on a 2018 Teklad Global 18% Protein Rodent Diet (Harlan, San Diego, Calif., USA) and water throughout the study period.

Formulation Administration

Food was removed from the cage the evening prior to surgery. Rats had ad lib access to drinking water while in the home cage the evening prior to surgery. Following anesthesia, an incision was made in the midline of the abdomen for isolation of the small intestine. Rats were administered 17 mL of either Representative Formulation 2 or Comparative Formulation 2 via direct injection into the intestine using a 30 gauge needle. Following formulation administration, the rats were subjected to experimentally induced shock via the SMAO procedure.

Anesthesia and Preoperative Preparation

Animals were anesthetized with ketamine/xylazine (75/4 mg/kg, I.M.). Supplemental anesthesia (ketamine/xylazine 10% initial dose, I.M.) was administered as indicated following response to tail/toe pinch. Anesthesia was maintained throughout the experimental shock period.

Rats were secured in a supine position to a temperature controlled (water circulating heat pump) operating table. The animals were maintained at 37° C. throughout the procedures.

All surgical procedures were performed using aseptic techniques. Sterile drapes, heat sterilized instruments, and surgical apparel (gown, face mask, and gloves) were used. The surgical sites on the abdomen and left groin were shaved and cleaned with betadine followed by 70% alcohol.

SMAO Procedures

To initiate the model, following anesthesia the superior mesenteric artery was located and tied off (occluded) to prevent blood flow to the intestine and initiate a 30 minute shock/hypoperfusion period. The surgical site was covered with moistened sterile gauze during the entire SMAO shock period. After the 30 minute period, the SMAO was untied (occlusion removed). Perfusion was resumed for a period of 2 hours, followed by sacrifice of the animals.

Necropsy and Histological Processing

The intestines were then harvested by tying off both ends, injecting a 10% neutral buffered formalin solution with a 30 gauge needle, and storing the intestines in a jar filled with 10% neutral buffered formalin.

Following at least 24 hours of incubation in formalin, an approximate 5 cm by 5 cm section of the ileum (at approximately ⅚ the length of the small intestine) was excised for structural analysis. The tissue sample was adhered to a cardboard backing and mounted for sectioning. Intestinal cross sections of 15-20 microns thickness were created on a Vibratome Series 3000 sectioning system. Free floating sections were washed overnight in water to remove formalin. Sections were then free floating stained with Alcian blue (pH 2.5) (Diagnostic BioSystems, Catalog No. KT 003) and mounted on slides for analysis.

Tissue Analysis

A Leitz Wetzlar Dialux 20 microscope (Wetzlar, West Germany) and 20× objective was used to image tissue sections. Still images of the tissue were captured with a Spot Insight Gigabit Camera, Model No. 35.2, Diagnostic Instruments, Inc. (Sterling Heights, Mich.) and included software. Images were stored as TIFF files with no compression used. Images were loaded into Photoshop Elements 13 and enhanced to sharpen the contours of the villi. To quantify the extent of damage to the villi, villi were classified as damaged when either of the following criteria were met:

1) Villi tips were broken away or structural damage to any portion of the villi; or
2) Goblet cells (normally stained blue) were practically non-existent (≤3 goblet cells with no stain) from the base to the villi tip The Photoshop Text tool was used to place an n (for no damage) or a d (for damage) in proximity to each individual villi for each tissue cross section. Where a determination of damage was inconclusive, the villi were excluded from the analysis. These inconclusive villi were less than 5% of the total villi analyzed. An image demonstrating the identification methodology is in FIG. 1, which shows a cross section of the small intestine from a rat treated with an enteral formulation. Healthy villi are marked with n and damaged villi are marked with d.

Results

Figure 4A:
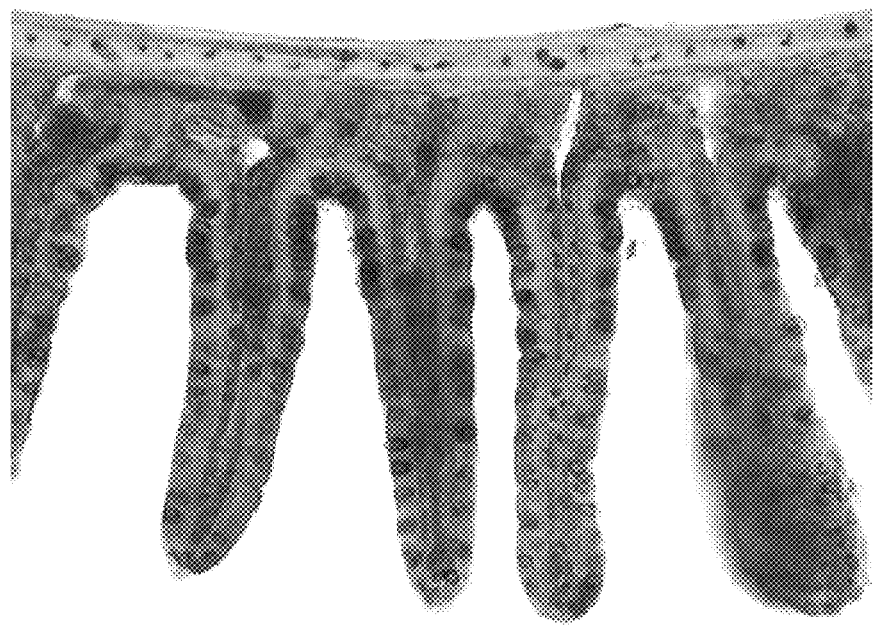
FIGS. 4A and 4B show the cross section of the small intestine from a rat treated with Representative Formulation 2 and Comparative Formulation 2, respectively.
Figure 4B:
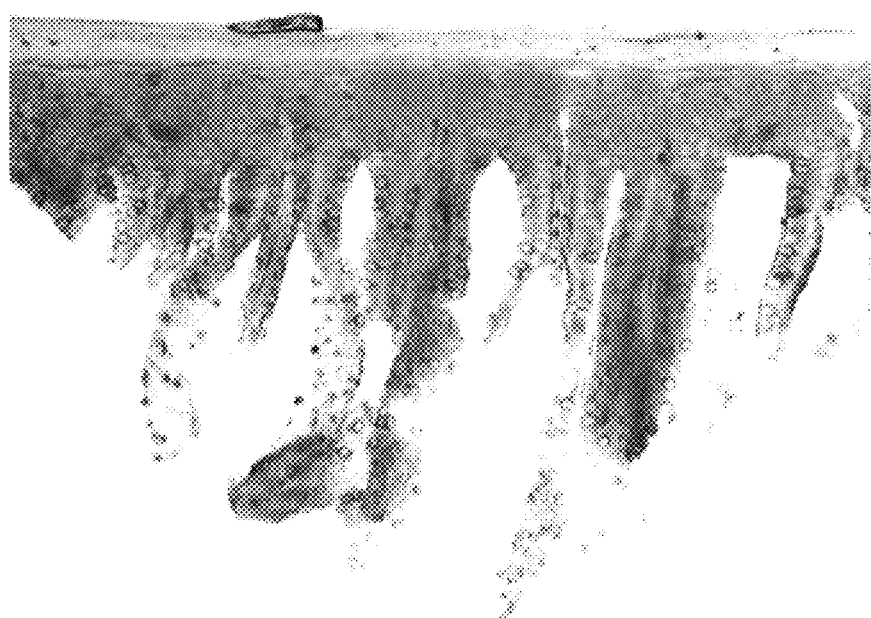

A total of eight rats were tested. Four rats received Representative Formulation 2 by direct enteral injection, and four rats received Comparative Formulation 2 by direct enteral injection. Representative micrographs of the villi after administration of the formulations and shock induction are shown in FIGS. 4A and 4B. FIG. 4A shows a cross section of the small intestine of a rat treated with Representative Formulation 2. The villi in FIG. 4A appear healthy and structurally intact as the entire length of the villi are visible and completely covered in goblet cells. FIG. 4B shows a cross section of the small intestine of a rat treated with Comparative Formulation 2. The villi in FIG. 4B appear to be structurally damaged with missing villi tips and atypical goblet cell staining.

Figure 5:
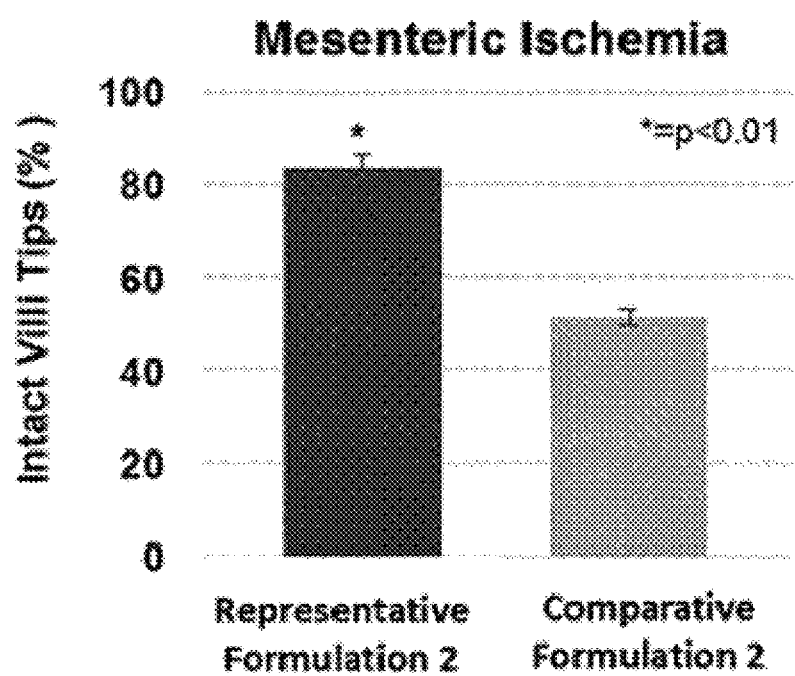
FIG. 5 illustrates the percentage of villi that were structurally intact with intact epithelial lining in all rats treated in Example 3. Representative Formulation 2 preserved on average 83.4% of villi, while Comparative Formulation 2 preserved on average 51.3% of the villi. Data are averages±SEM; n=4 rats in each group; *=$p<0.01$ compared to respective treated group, ANOVA.

Quantification of villi that are structurally intact after administration of the formulations and shock induction are shown in Tables 7 and 8 and FIG. 5. Table 7 shows the individual rat data for the quantification of the structurally intact villi. Table 8 summarizes the total intact villi and damaged villi observed after administration of the formulations and shock induction. FIG. 5 shows the mean percentage of villi intact per rat after administration of the formulations and shock induction. 83.4% of villi were intact across all rats that received Representative Formulation 2, whereas only 51.3% of the villi were intact across all rats that received Comparative Formulation 2. These results are consistent with the mean values calculated from the total villi observed in Table 8.

TABLE 7

| Rats Treated with Representative Formulation 2 | % Intact Villi | Rats Treated with Comparative Formulation 2 | % Intact Villi |
|---|---|---|---|
| Rat #1 | 85.3% | Rat #2 | 46.3% |
| Rat #4 | 88.2% | Rat #3 | 54.1% |
| Rat #6 | 76.0% | Rat #5 | 51.3% |
| Rat #8 | 84.2% | Rat #7 | 53.7% |
| Mean | 83.4% | Mean | 51.3% |
| SEM (+/−) | 2.6% | SEM (+/−) | 1.8% |

TABLE 8

|  | Rats Treated with Representative Formulation 2 | Rats Treated with Comparative Formulation 2 |
|---|---|---|
| Number of Intact Villi | 110 | 106 |
| Number of Damaged Villi | 21 | 102 |
| Total Villi | 131 | 208 |
| % Intact | 84.0% | 51.0% |

Example 4

Hemorrhagic Shock Studies with Formulations Administered Via Direct Stomach Injection The hemorrhagic shock model was used to assess the ability of a representative composition comprising PEG 3350 (Representative Formulation 3) and a comparative composition without PEG 3350 (Comparative Formulation 3) to preserve the structural integrity of the gastrointestinal tract under hemorrhagic conditions when administered by direct stomach injection.

Formulation Preparation

The materials used to prepare the formulations and their sources are shown in Table 9. All materials used were USP grade. As shown in Table 9, the Representative Formulation 3 comprises tranexamic acid, electrolytes, PEG 3350, and glucose, and Comparative Formulation 3 comprises tranexamic acid, electrolytes, and glucose.

TABLE 9

| Component | Representative Formulation 3 | Comparative Formulation 3 | Source |
|---|---|---|---|
| Tranexamic acid | 0.043 g | 0.043 g | Daiichi Sankyo |
| PEG 3350 | 0.287 g | 0.0 g | OTC clinical grade Miralax |
| Sodium Sulfate (Anhydrous) | 0.033 g | 0.033 g | Sigma-Aldrich |
| Sodium Bicarbonate | 0.010 g | 0.010 g | Sigma-Aldrich |
| Sodium Chloride | 0.009 g | 0.009 g | Sigma-Aldrich |
| Potassium Chloride | 0.004 g | 0.004 g | Sigma-Aldrich |
| Glucose | 0.229 g | 0.229 g | Sigma-Aldrich |
| Water | 3.629 g | 3.629 g | Sterile water for injection |
| Total Solution | 4.000 mL | 4.000 mL |  |

Rats and Diet

Male WISTAR rats with a weight of 320-400 grams were purchased from Charles River Laboratories, located in Wilmington, Mass. All rats were maintained on Charles River Laboratories feed and provided water ad libitum throughout the study period.

Formulation Administration

Food was removed from the cage the evening prior to surgery. After placement of catheters, a small skin incision in the abdomen was made for isolation of the stomach. Following stabilization after experimentally induced shock via the hemorrhagic shock procedure, rats were administered 4 mL of either Representative Formulation 3 or Comparative Formulation 3 via a direct injection into the middle of the stomach.

Anesthesia and Preoperative Preparation

Animals were anesthetized with ketamine (75 mg/kg, I.M.). Anesthesia was maintained throughout the experimental shock period.

Rats were secured in a supine position to a temperature controlled (water circulating heat pump) operating table. The animals were maintained at 37° C. throughout the procedures. Vital signs (systemic blood pressure or respiratory rate, body temperature) were monitored throughout the procedures.

All surgical procedures were performed using aseptic techniques. Sterile drapes, heat sterilized instruments, and surgical apparel (gown, face mask, and gloves) were used. The surgical sites on the abdomen and left groin were shaved and cleaned with betadine followed by 70% alcohol.

Hemorrhagic Shock Procedures

To initiate the model, rats were anesthetized with ketamine (75 mg/kg, I.M.). Abdominal and inguinal regions were shaved and disinfected with alcohol. The right femoral artery was cannulated. The surgical site was covered with moistened sterile gauze during entire hemorrhagic shock period. Hemorrhagic shock was initiated by reduction of blood volume (about 40% of whole blood volume based on 6% body weight) to achieve a blood pressure of 35 mmHg (47.58 cm $H_2O$) for a period of 2 hours. Briefly, each rat was heparinized with minimal concentrations of sodium heparin (0.5 USP units/ml of blood volume estimated as 6% body weight) to prevent blood coagulation during the procedure. The right femoral artery was connected with a 10 cc syringe. About 6 ml of blood was withdrawn from the femoral artery over a period of about 5-10 minutes. The syringe was then placed at 47.58 cm high above the rat body level. The syringe served as a blood reservoir that regulated blood pressure at 47.58 cm $H_2O$ (35 mm Hg) automatically. If the blood pressure was above 47.58 cm H2O, blood flowed into the blood reservoir. If the blood pressure was under 47.58 cm $H_2O$, the blood from the blood reservoir was infused into blood stream circulation. Once mean arterial pressure (MAP) was stabilized, either Representative Formulation 3 or Comparative Formulation 3 was injected into the middle of the stomach.

Necropsy and Histological Processing

The intestines were then harvested by tying off both ends, injecting a 10% neutral buffered formalin solution with a 30 gauge needle, and storing the intestines in a jar filled with 10% neutral buffered formalin.

Following at least 24 hours of incubation in formalin, an approximate 5 cm by 5 cm section of the ileum (at approximately ⅝ the length of the small intestine) was excised for structural analysis. The tissue sample was adhered to a cardboard backing and mounted for sectioning. Intestinal cross sections of 15-20 microns thickness were created on a Vibratome Series 3000 sectioning system. Free floating sections were washed overnight in water to 2remove formalin. Sections were then free floating stained with Alcian blue (pH 2.5) (Diagnostic BioSystems, Catalog No. KT 003) and mounted on slides for analysis.

Tissue Analysis

A Leitz Wetzlar Dialux 20 microscope (Wetzlar, West Germany) and 20× objective was used to image tissue sections. Still images of the tissue were captured with a Spot Insight Gigabit Camera, Model No. 35.2, Diagnostic Instruments, Inc. (Sterling Heights, Mich.) and included software. Images were stored as TIFF files with no compression used. Images were loaded into Photoshop Elements 13 and enhanced to sharpen the contours of the villi. To quantify the extent of damage to the villi, villi were classified as damaged when either of the following criteria were met:

1) Villi tips were broken away or structural damage to any portion of the villi; or
2) Goblet cells (normally stained blue) were practically non-existent (≤3 goblet cells with no stain) from the base to the villi tip The Photoshop Text tool was used to place an n (for no damage) or a d (for damage) in proximity to each individual villi for each tissue cross section. Where a determination of damage was inconclusive, the villi were excluded from the analysis. These inconclusive villi were less than 5% of the total villi analyzed. An image demonstrating the identification methodology is in FIG. 1, which shows a cross section of the small intestine from a rat treated with an enteral formulation. Healthy villi are marked with n and damaged villi are marked with d.

Results

Figure 6A:
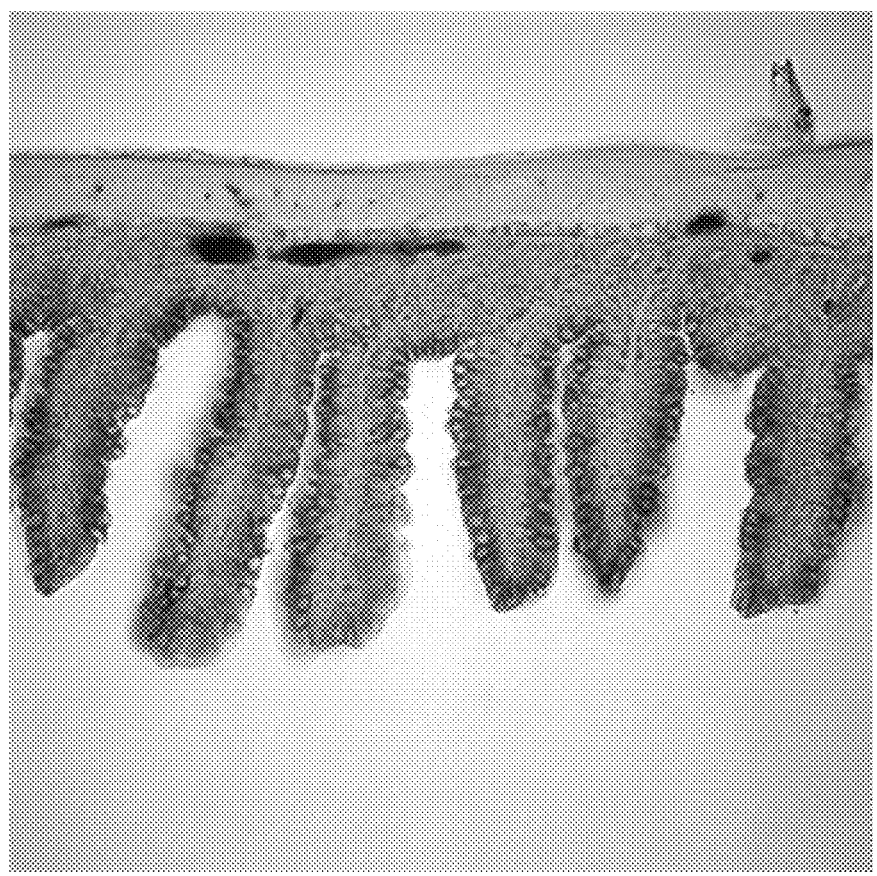
FIGS. 6A and 6B show the cross section of the small intestine from a rat treated with Representative Formulation 3 and Comparative Formulation 3, respectively.
Figure 6B:
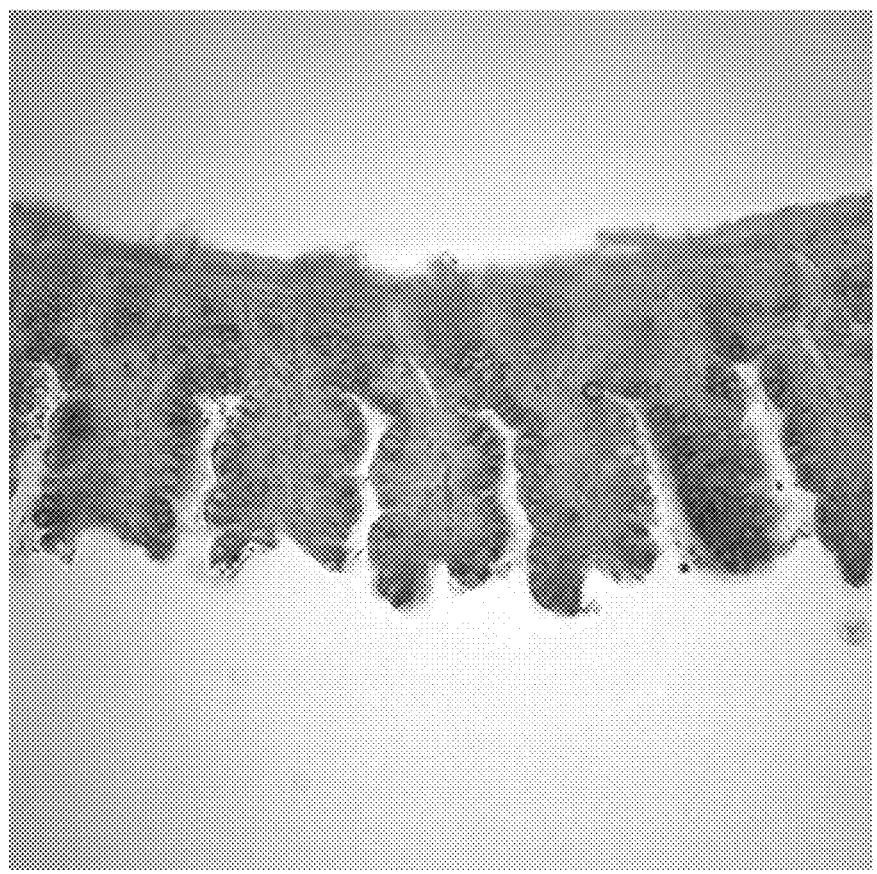

A total of eight rats were tested. Four rats received Representative Formulation 3 by direct stomach injection, and four rats received Comparative Formulation 3 by direct stomach injection. Representative micrographs of the villi after administration of the formulations and shock induction are shown in FIGS. 6A and 6B. FIG. 6A shows a cross section of the small intestine of a rat treated with Representative Formulation 3. The villi in FIG. 6A appear healthy and structurally intact as the entire length of the villi are visible and completely covered in goblet cells. FIG. 6B shows a cross section of the small intestine of a rat treated with Comparative Formulation 3. The villi in FIG. 6B appear to be structurally damaged.

Figure 7:
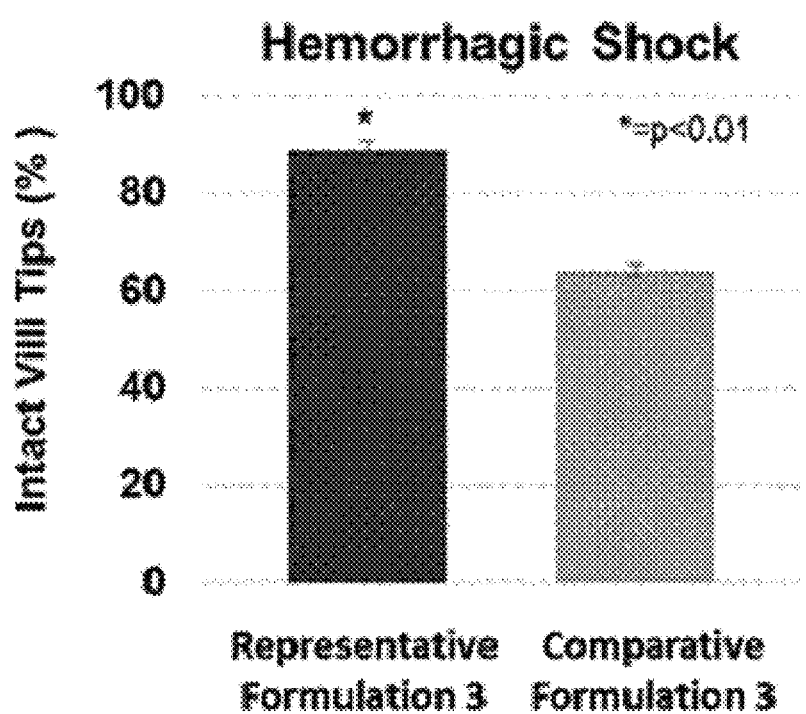
FIG. 7 illustrates the percentage of villi that were structurally intact with intact epithelial lining in all rats treated in Example 4. Representative Formulation 3 preserved on average 88.8% of villi, while Comparative Formulation 3 preserved on average 64.1% of the villi. Data are averages±SEM; n=4 rats in each group; *=$p<0.01$ compared to respective treated group, ANOVA.

Quantification of villi that are structurally intact after administration of the formulations and shock induction are shown in Tables 10 and 11 and FIG. 7. Table 10 shows the individual rat data for the quantification of the structurally intact villi. Table 11 summarizes the total intact villi and damaged villi observed after administration of the formulations and shock induction. FIG. 7 shows the mean percentage of villi intact per rat after administration of the formulations and shock induction. 88.8% of villi were intact across all rats that received Representative Formulation 3, whereas only 64.1% of the villi were intact across all rats that received Comparative Formulation 3. These results are consistent with the mean values calculated from the total villi observed in Table 11.

TABLE 10

| Rats Treated with Representative Formulation 3 | % Intact Villi | Rats Treated with Comparative Formulation 3 | % Intact Villi |
| --- | --- | --- | --- |
| Rat #701 | 90.7% | Rat #802 | 65.6% |
| Rat #704 | 83.3% | Rat #805 | 66.7% |
| Rat #705 | 91.1% | Rat #806 | 62.7% |
| Rat #706 | 90.0% | Rat #807 | 61.5% |
| Mean | 88.8% | Mean | 64.1% |
| SEM (+/−) | 1.8% | SEM (+/−) | 1.2% |

TABLE 11

|  | Rats Treated with Representative Formulation 3 | Rats Treated with Comparative Formulation 3 |
| --- | --- | --- |
| Number of Intact Villi | 171 | 105 |
| Number of Damaged Villi | 23 | 59 |
| Total Villi | 194 | 164 |
| % Intact | 88.1% | 64.0% |

Example 5

Clinical Study for the Treatment of Septic Shock

Primary Objective

This is a multicenter, randomized, double-blind, parallel, placebo-controlled Phase 2 clinical study of septic shock patients to determine whether enteral administration of a formulation comprising tranexamic acid, PEG, glucose, and one or more electrolytes increases the number of days alive without cardiovascular, pulmonary, or renal replacement therapy through Day 28 compared to Placebo.

Secondary Objectives

The secondary safety objective of this study is to assess safety and tolerability of experimental composition in patients with septic shock.

Eligibility

1. First episode of documented or suspected sepsis of peritoneal/abdominal, soft tissue, blood, or community acquired lung origin.
2. Must have septic shock requiring vasopressors despite adequate fluid resuscitation of 30 mL/kg crystalloid or colloid equivalent, for either an SBP≤90 mmHg or a MAP≤65 mmHg (i.e. must have been unable to maintain adequate blood pressure despite adequate fluid resuscitation).

3. Age 18 to 75 years

Study Design

The study is composed of four periods:

Screening: This period begins when the patient has documented or suspected sepsis of peritoneal/abdominal, soft tissue, blood, or community acquired lung origin and is unable to maintain adequate blood pressure (BP, systolic BP [SBP]>90 mmHg or a mean arterial pressure [MAP]>65 without vasopressor support) despite intravenous fluid resuscitation. Enteral study drug administration must start within 4 hours of randomization and no later than 24 hours after the onset of shock.

Intervention: This period begins with the first administration of the test formulation or placebo and continues throughout treatment duration, up to 8 days pending patient refusal to take study drug, exit from hospital or death. There are no food or fluid restrictions. However, during the first 48 hours following enrollment, physicians are encouraged to delay enteral nutrition. If a patient is moved from ICU and still in the hospital, study drug administration should continue until 8 doses have been administered.

Post-intervention: This period begins after study drug administration is complete and continues through Study Day 28 or until the patient is discharged from the hospital (if before Day 28). If a patient has been discharged from the study hospital before Study Day 28, site personnel will contact the patient or surrogate, caregiver, family member, physician, or healthcare facility to obtain the patient's survival status, organ support and functional outcome assessment.

Follow-up: Site personnel will contact the patient, surrogate, caregiver, family member, or patient's other healthcare providers to determine survival status on Day 90.

All randomized patients will be divided between the two treatment arms in a 1:1 ratio stratified by highest total SOFA score during the screening period (known at the time of randomization); and then by percent change in serum lactate between the first and subsequent lactate measurements (separated by at least 4 hours to be used to qualify for randomization).

A total of 250 patients are enrolled. The 700 mL aqueous solution formulation shown in Table 2 is administered orally or via a nasogastric, orogastric, nasojejunal, orojejunal, nasoduodenal, or percutaneous endoscopic gastrostomy tube or catheter to patients in the experimental arm. Patients in the placebo arm of the study receive 700 mL of a placebo solution that does not comprise tranexamic acid orally or via a nasogastric, orogastric, nasojejunal, orojejunal, nasoduodenal, or percutaneous endoscopic gastrostomy tube or catheter. Daily treatment is administered continuously or intermittently spread over an 8 to 24 hour period. 700 mL of experimental product or placebo is administered every 24 hours. Treatment is administered daily on Study Days 1-8, barring death or hospital discharge. Depending on the start time of the initial administration (infusion) on Study Day 1, the final administration extends into Study Day 9.

Efficacy Endpoints

The primary efficacy endpoint is the number of days alive without cardiovascular, renal, or pulmonary organ support through Day 28. Patients are classified as having organ support if organ support is required through the use of:

Mechanical ventilation;
Vasopressors to maintain adequate BP, or
Renal replacement therapy.

The secondary efficacy endpoint is mortality rate: Date of death will be recorded for all patients who have died on or before Study Day 90. The 7-day, 28-day, and 90-day mortality and survival rates will be evaluated.

Results

The aqueous solution formulation shown in Table 2 is safe and well-tolerated by patients in the experimental arm. Patients in the experimental arm exhibit an increase in the number of days without cardiovascular, renal, or pulmonary support through Day 28 of the study as compared to patients in the placebo arm. Patients in the experimental arm exhibit a decrease in the rates of mortality on day 90 of the study as compared to mortality rates of patients in the placebo arm.

Example 6

Clinical Study for the Treatment of Shock and Multiorgan Dysfunction after Cardiovascular Surgery Primary Objective This is a multicenter, randomized, double-blind, parallel, placebo-controlled, Phase 2 clinical study to determine whether enteral administration of a formulation comprising tranexamic acid, PEG, glucose, and one or more electrolytes prior to high risk cardiovascular surgery increases the number of days alive without cardiovascular, renal, or pulmonary dysfunction through Day 14 compared to Placebo.

Study Design

All high risk cardiovascular surgery randomized patients will be divided between the 2 treatment groups in a 1:1 ratio stratified by:

Age (≤64 or ≥65 years of age);
STS Cardiac Score, and
Procedure.

The study is composed of four periods:

Screening and randomization (not to exceed 4 weeks): prior to cardiovascular surgery.

Intervention: will begin with the first enteral administration of study drug 6-12 hours prior to surgery (Day 0). Treatment should continue for a minimum of 7 days (pending patient refusal to take study drug, exit from hospital, or mortality). In some cases, patients with continued organ dysfunction remain on study drug for up to 10 days as long as organ dysfunction persists.

Post-intervention in-hospital: will start after study drug administration is stopped (Day 8) and will continue through Day 14 or until the patient is discharged from the hospital.

Follow-up: the patient will be contacted by phone to assess functional outcomes at Day 28.

A total of 100 patients are enrolled. The 700 mL aqueous solution formulation shown in Table 2 or a Placebo that does not comprise tranexamic acid is administered orally or via a nasogastric, orogastric, nasojejunal, orojejunal, nasoduodenal, or percutaneous endoscopic gastrostomy tube or catheter to patients on Days 0-7. If a patient continues to demonstrate organ dysfunction, the physician will continue treatment for a maximum of 10 days for some cases. Patients, investigators, persons performing the assessments, and data analysts remain blinded to the identity of the treatment from time of randomization until database lock.

Efficacy Endpoints

The primary efficacy endpoint is the number of days alive without cardiovascular, renal or pulmonary organ support through Day 14. Patients are classified as requiring organ support if organ support is provided through the use of:
- Mechanical ventilation;
- Vasopressors to maintain adequate blood pressure (BP); or
- Renal replacement therapy (hemodialysis, peritoneal dialysis or continuous venous hemofiltration).

The secondary efficacy endpoint is mortality rate: date of death will be recorded for all patients who have died on or before Study Day 28 and Day 90. The 28-day and 90-day mortality and survival rates will be evaluated.

Results

The aqueous solution formulation shown in Table 2 is safe and well-tolerated by patients in the experimental arm. Patients in the experimental arm exhibit an increase in the number of days alive without cardiovascular, renal, or pulmonary dysfunction through Day 14 compared to Placebo. Patients in the experimental arm exhibit a decrease in the rates of mortality on day 90 of the study as compared to mortality rates of patients in the placebo arm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are employed in practicing the invention. It is intended that the following claims define the scope of the invention and that methods and structures within the scope of these claims and their equivalents be covered thereby.

What is claimed is:

1. A composition comprising about 7.5 g of tranexamic acid, about 32.5 g to about 50.3 g of PEG 3350, about 28 g to about 40 g of glucose, about 4.0 g to about 5.7 g of sodium sulfate, about 1.2 g to about 1.7 g of sodium bicarbonate, about 1.0 g to about 1.5 g of sodium chloride, and about 0.5 g to about 0.7 g of potassium chloride.

2. The composition of claim 1, comprising about 7.5 g of tranexamic acid, about 32.5 g of PEG 3350, about 28 g of glucose, about 4.0 g of sodium sulfate, about 1.2 g of sodium bicarbonate, about 1.0 g of sodium chloride, and about 0.5 g of potassium chloride.

3. The composition of claim 1, comprising about 7.5 g of tranexamic acid and about 28 g of glucose.

4. The composition of claim 1, formulated as about 700 mL of an aqueous solution.

5. An aqueous composition comprising about 1.1 wt % of tranexamic acid, about 4.2 wt % to about 5.1 wt % of PEG 3350, about 3.6 wt % to about 4.4 wt % of glucose, about 0.51 wt % to about 0.63 wt % of sodium sulfate, about 0.16 wt % to about 0.19 wt % of sodium bicarbonate, about 0.13 wt % to about 0.17 wt % of sodium chloride, and about 0.06 wt % to about 0.09 wt % of potassium chloride.

6. The composition of claim 5, comprising about 4.6% w/v of PEG 3350, and about 4.0% w/v of glucose.

7. The composition of claim 6, comprising about 0.6% w/v of sodium sulfate, about 0.2% w/v of sodium bicarbonate, about 0.1% w/v of sodium chloride, and about 0.1% w/v of potassium chloride.

8. The composition of claim 6, comprising about 0.57% w/v of sodium sulfate, about 0.17% w/v of sodium bicarbonate, about 0.15% w/v of sodium chloride, and about 0.07% w/v of potassium chloride.

9. The composition of claim 5, formulated as about 700 mL of an aqueous solution.

10. A method of increasing a number of intact intestinal villi in a subject suffering from intestinal ischemia, the method comprising administering an effective amount of the composition of claim 1 thereby increasing the number of intact intestinal villi in the subject relative to the absence of administering an effective amount of the composition of claim 1.

11. A method of increasing a number of intact intestinal villi in a subject suffering from intestinal ischemia, the method comprising administering an effective amount of the composition of claim 5 thereby increasing the number of intact intestinal villi in the subject relative to the absence of administering an effective amount of the composition of claim 5.

* * * * *